United States Patent
Lu et al.

(10) Patent No.: US 9,125,863 B2
(45) Date of Patent: Sep. 8, 2015

(54) SYNERGISTIC IMMUNOGENIC FUSION PROTEIN-POLYSACCHARIDE CONJUGATE

(75) Inventors: Ying-jie Lu, Chestnut Hill, MA (US); Richard Malley, Beverly, MA (US)

(73) Assignee: Children's Medical Center Corporation, Boston, MA (US)

(*) Notice: Subject to any disclaimer, the term of this patent is extended or adjusted under 35 U.S.C. 154(b) by 930 days.

(21) Appl. No.: 12/992,282

(22) PCT Filed: May 22, 2009

(86) PCT No.: PCT/US2009/044956
§ 371 (c)(1),
(2), (4) Date: Jan. 28, 2011

(87) PCT Pub. No.: WO2009/143413
PCT Pub. Date: Nov. 26, 2009

(65) Prior Publication Data
US 2011/0206716 A1   Aug. 25, 2011

Related U.S. Application Data

(60) Provisional application No. 61/055,173, filed on May 22, 2008, provisional application No. 61/156,973, filed on Mar. 3, 2009, provisional application No. 61/164,605, filed on Mar. 30, 2009.

(51) Int. Cl.
*A61K 39/00*   (2006.01)
*A61K 39/09*   (2006.01)

(52) U.S. Cl.
CPC ......... *A61K 39/092* (2013.01); *A61K 2039/543* (2013.01); *A61K 2039/55505* (2013.01); *A61K 2039/6068* (2013.01); *A61K 2039/6087* (2013.01); *C07K 2319/00* (2013.01)

(58) Field of Classification Search
CPC ................................................ C07K 2319/00
See application file for complete search history.

(56) References Cited

U.S. PATENT DOCUMENTS

| 2005/0070695 A1 | 3/2005 | Minetti et al. | |
|---|---|---|---|
| 2009/0017072 A1* | 1/2009 | Biemans et al. | 424/244.1 |
| 2012/0237542 A1* | 9/2012 | Hausdorff et al. | 424/197.11 |
| 2014/0154286 A1* | 6/2014 | Malley et al. | 424/190.1 |

FOREIGN PATENT DOCUMENTS

| CN | 1899609 A | * | 1/2007 |
|---|---|---|---|
| EP | 1834650 A1 | * | 12/2005 |
| EP | 1834650 A1 | | 9/2007 |
| WO | WO 2005/108580 A1 | * | 11/2005 |
| WO | 2007/081583 | | 7/2007 |
| WO | 2007/144647 | | 12/2007 |
| WO | WO 2009/020553 | * | 2/2009 |

OTHER PUBLICATIONS

Kuo et al., Infection and Immunity, 1995; 63(7): 2706-2713.*
Giefing et al., JEM, Jan. 2008; 205(1): 117-131.*
Kuberan et al., Current Organic Chemistry, 2000; 4: 653-677.*
Bowie et al. (Science, 1990, 257:1306-1310).*
Basset et al., Infect. Immun., 75(11):5460-5464 (2007). "Antibody-independent, CD4+ T-cell-dependent protection against pneumococcal colonization elicited by intranasal immunization with purified pneumococcal proteins.".
Ho et al., Immunopharmacology, 46(1), Abstract only (2000). "The immunostimulating activities of anti-tumor polysaccharide from K1 capsular (polysaccharide) antigen isolated from *Klebsiella pneumoniae*.".
Ogunniyi et al., Infect. Immun., 69(10:5997-6003 (2001). "Protection against *Streptococcus pneumoniae* elicited by immunization with pneumolysin and CbpA.".
Blander et al., "Toll-dependent selection of microbial antigens for presentation by dendritic cells" Nature 440:808-812 (2006).
Briles et al., "The potential for using protein vaccines to protect against otitis media caused by *Streptococcus pneumoniae*" Vaccine 19:S87-S95 (2000).
Huleatt et al., "Vaccination with recombinant fusion proteins incorporating toll-like receptor ligands induces rapid cellular and humoral immunity" Vaccine 25:763-775 (2006).
Ishii et al., "Toll or toll-free adjuvant path toward the optimal vaccine development" Journal of Clinical Immunology 27:363-371 (2007).
Kim et al., "Lipoteichoic acid and muramyl dipeptide synergistically induce maturation of human dendritic cells and concurrent expression of proinflammatory cytokines" Journal of Leukocyte Biology 81:983-989 (2007).
Lu et al., "Protection against pneumococcal colonization and fatal pneumonia by a trivalent conjugate of a fusion protein with the cell wall polysaccharide" Infection and Immunity 77:2076-2083 (2009).
Malley et al., "Antibody-independent, interleukin-17A-mediated, cross-serotype immunity to pneumococci in mice immunized intranasally with the cell wall polysaccharide" Infection and Immunity 74:2187-2195 (2006).
Malley et al., "Recognition of pneumolysin by toll-like receptor 4 confers resistance to pneumococcal infection" Proceedings of the National Academy of Sciences 100:1966-1971 (2003).
Supplementary European Search Report, EP09751641, dated Mar. 6, 2013.

* cited by examiner

*Primary Examiner* — Gary Nickol
*Assistant Examiner* — Lakia Tongue
(74) *Attorney, Agent, or Firm* — Nixon Peabody LLP

(57) ABSTRACT

An immunogenic composition comprising a fusion protein-polysaccharide conjugate consisting of a polysaccharide (PS) or pneumococcal bacterial cell wall polysaccharide (CWPS) conjugated to X:PdT where PdT represents the nonhemolytic variant of pneumolysin and X represents an antigenic peptide or protein of interest is provided. The immunity to X is synergistically enhanced by the fusion conjugate. Methods of protecting a subject from pneumococcal colonization or disease by administering an immunogenic composition including a fusion protein (PsaA:PdT) containing truncated PsaA and the nonhemolytic variant of pneumolysin (PdT) conjugated with CWPS (PsaA:PdT-CWPS) is also provided.

9 Claims, 18 Drawing Sheets

SYNERGISTIC IMMUNOGENIC FUSION PROTEIN-POLYSACCHARIDE CONJUGATE

CROSS REFERENCE TO RELATED APPLICATIONS

This application is a 35 U.S.C. §371 National Phase Entry application of International Application No. PCT/US2009/044956 filed on May 22, 2009, which designates the United States, and which claims the benefit of priority under 35 U.S.C. §119(e) of U.S. Provisional Application No. 61/055,173, filed May 22, 2008; U.S. Provisional Application No. 61/156,973, filed Mar. 3, 2009; and U.S. Provisional Application No. 61/164,605, filed Mar. 30, 2009, the contents of each of which are incorporated by reference herein in their entirety.

This invention was made with government support under grants No. AI067737-01 and No. AI51526-01, awarded by the National Institutes of Health. The U.S. government has certain rights in the invention.

FIELD OF THE INVENTION

The present invention relates to molecular genetics, immunology, and bacteriology. More specifically, an embodiment of the present invention provides for an immunogenic fusion conjugate comprising a fusion protein consisting of a protein or peptide of interest (for example, a truncated pneumococcal surface adhesin A protein) and a nonhemolytic pneumolysin protein, conjugated to a polysaccharide, such as dextran or a pneumococcal cell wall polysaccharide. This fusion conjugate confers a synergistic, immunogenic, humoral and cellular response, and in the case of pneumococci elicits synergistic, antibody- and cell- (including IL-17A)-mediated, protection against lethal infection and mucosal pneumococcal colonization.

BACKGROUND OF THE INVENTION

Globally, infectious diseases cause over 13 million deaths each year, and cancers cause over 12 million deaths each year. For example, infection with *Streptococcus pneumoniae* is a major cause of morbidity and mortality worldwide and can lead to pneumonia, meningitis and bacteraemia, and some less severe infections such as otitis media. Almost one million children in the developing world die of infections due to *S. pneumoniae* (more commonly known as pneumococcus) each year. Antibiotics offer effective treatment for many cases of pneumococcal disease. The rapid emergence of multiple-drug-resistant strains of *S. pneumoniae*, however, has limited the effectiveness of antibiotics and stimulated renewed interest in the prevention of pneumococcal infections with vaccines.

The success of passive immunization and polysaccharide-based vaccines for the prevention of colonization and/or disease has demonstrated the importance of capsular antibodies in controlling pneumococcal disease and colonization. Furthermore, studies in both animals and humans demonstrate that these antibodies can protect against nasopharyngeal (NP) pneumococcal colonization, which precedes pneumococcal disease. The importance of this effect has become clear and has paralleled what was learned after universal immunization with *Haemophilus influenzae* type b vaccine: in the U.S., the pneumococcal conjugate vaccine has prevented more than twice as many cases of invasive pneumococcal disease through indirect effects on pneumococcal transmission (i.e., herd immunity) as through its direct effect of protecting vaccinated children.

Protection by anticapsular antibody is limited by its serotype specificity: The 7-valent pneumococcal conjugate vaccine (PCV7) has significantly reduced the incidence of invasive pneumococcal disease due to vaccine-type (VT) strains. Recent studies have shown, however, that non-VT serotypes in PCV7 are gradually replacing VT, potentially limiting the usefulness of the vaccine. This has led to the evaluation of whether pneumococcal colonization can be prevented by immunization with conserved antigens. In particular, several pneumococcal proteins have been evaluated as vaccine candidates in animal models of pneumococcal colonization. Mucosal immunization with some of these proteins has been shown to elicit systemic and mucosal antibodies and to confer protection against pneumococcal disease and colonization. There remains a need for an immunogenic composition, including pneumococcal polysaccharides and proteins, that raises antibodies and a robust cellular and humoral immune response to all serotypes.

The innate immune response provides rapid and usually effective defense against microbial pathogens. This response involves recognition of pathogen-associated molecules, triggering production and release of inflammatory mediators, recruitment of leukocytes, and activation of antimicrobial effectors. The Toll-like receptors (TLRs), of which at least eleven have been described for mammals, are capable of discriminating among a wide variety of pathogen-associated molecules and eliciting protective responses. TLR4 recognizes microbial products from organisms including gram-negative bacteria, the F protein of respiratory syncytial virus, and cholesterol-dependent cytolysins (CDC) of gram-positive bacteria. Hence, there remains a need to harness the TLR4 mechanism in eliciting an immune response against infections such as pneumococcal colonization and disease.

SUMMARY OF THE INVENTION

The present invention relates to immunogenic compositions comprising a fusion protein, X:PdT, where PdT represents a nonhemolytic variant of pneumolysin and X represents a peptide/protein of interest, conjugated to a polysaccharide (PS) such as dextran or pneumococcal cell wall polysaccharide (CWPS) (X:PdT-PS), such that humoral and cellular/mucosal immunity to protein X is enhanced.

An embodiment of the present invention provides for an immunogenic conjugate comprising a fusion protein of a truncated pneumococcal PsaA protein and a nonhemolytic pneumolysin protein, conjugated to a pneumococcal cell wall polysaccharide. This conjugate vaccine confers synergistic TLR4-dependent, IL-17A-mediated protection against pneumococcal colonization and also confers significant protection against lethal pneumonia. Importantly, CWPS, pneumolysin and pneumococcal surface adhesin A (PsaA) are conserved in all serotypes and are important antigens for protection against *S. pneumoniae*. Additionally, as shown herein, protection against colonization in mice may be mediated by $T_H17$ cells and correlates with IL-17A expression from whole blood cells stimulated with pneumococcal antigens. The present invention provides for enhanced systemic $T_H17$ activity, increased antibody levels, and protection from pneumococcal lethal infection and colonization following immunization with the PsaA:PdT-CWPS fusion conjugates of these antigens in mice.

In a particular embodiment, a fusion protein (PsaA:PdT) containing truncated PsaA (amino acid residues 22-309) and a nonhemolytic variant of pneumolysin (PdT) (W433F, D385N, and C428G) was constructed, grown in and purified from E. coli, then conjugated with CWPS. Analysis of this conjugate showed retention of the TLR4 stimulatory property of PdT. More specifically, mice were immunized intranasally, twice at a weekly interval with 1 µg cholera toxin (CT) as adjuvant. Mice were bled three weeks after the last immunization and challenged intranasally with a serotype 6B strain the following week; density of colonization was determined seven days later by plating dilutions of tracheal washes. Mice immunized with the fusion protein conjugate had significantly increased IL-17A expression following pneumococcal stimulation compared with mice that received a protein plus polysaccharide antigen mixture. Further, the fusion conjugate PsaA:PdT-CWPS significantly protected mice against colonization compared with mice immunized with a simple mixture of the three antigens (mixture of PsaA, PdT, and CWP at the same molar ratios as in the fusion conjugate), who were not protected. In contrast to C3FI/HeOuJ mice (wild-type), C3H/HeJ (TLR4 mutant) mice were not protected by the PsaA:PdT-CWPS conjugate, implying that TLR4 plays an important role in protection. The present invention thus provides for a new vaccine candidate that is antigenically common to all serotypes and confers TLR4-dependent protection against pneumococcal colonization.

Moreover, the efficacy of the conjugate PsaA:PdT-CWPS mixed in alum vs. mixture in alum was tested in subcutaneous (s.c.) delivery to mice. Control groups included alum alone, WCV (given intranasally) and anticapsular antibodies given passively (to mimic the effect of a conjugate vaccine). Mice were challenged subsequently either nasally (to evaluate the effect on colonization) or by aspiration (to evaluate protection against sepsis and pneumonia). The conjugate was significantly more immunogenic than a mixture when given s.c. There was a 90% reduction in density of colonization by s.c. immunization with conjugate in alum vs. alum alone. Importantly, in aspiration challenge (sepsis) model, the conjugate was 100% protective against death, whereas mixture was non protective. Thus, the present invention provides for a conjugate vaccine that, with s.c. administration, is significantly more protective than an antigen mixture.

Additionally, the immunogenicity of one of the components of the fusion (PsaA) may be enhanced by combining it to CWPS and PdT. Therefore, other proteins of interest against which one wants to elicit an immune response may be incorporated as one part of the protein fusion. The invention thus relates to an immunogenic conjugate consisting of CWPS conjugated to X:PdT, where X represents any protein of interest, whether or not it is pneumococcal, so that an immune response against X is enhanced. In particular embodiments, X may be PsaA, StkPR, PcsB, or StkP. The data presented herein show that the immunogenicity of X is enhanced when X is presented as a synergistic fusion with PdT conjugated to CWPS, as opposed to when X is presented in a mixture of X, CWPS, and PdT antigens.

An embodiment of the present invention provides for an immunogenic composition comprising a fusion protein polysaccharide conjugate (X:PdT-PS) wherein X is an antigen, PdT is a nonhemolytic variant of pneumolysin, PS is a polysaccharide, wherein administration of said composition to a subject elicits enhanced humoral immunity, enhanced cellular immunity, and enhanced mucosal immunity. In one aspect of the embodiment, the PS has a molecular mass of <500 kDa. In another aspect of the embodiment, the PS has a molecular mass of <70 kDa.

Another embodiment of the present invention provides for an immunogenic composition comprising a fusion protein polysaccharide conjugate consisting of a polysaccharide conjugated to a X:PdT fusion protein where PdT is a nonhemolytic variant of pneumolysin and X is a target protein, such that immunity to X is enhanced. The polysaccharide may be dextran, Vi polysaccharide of Salmonella typhi, or pneumococcal cell wall polysaccharide (CWPS), or another polysaccharide of prokaryotic or eukaryotic origin.

In one aspect of the invention, X is an antigen derived from Staphylococci, Streptococci, Brucella, Enterococci species; Listeria, Bacillus, Corynebacteria, Neisseria meningitidis, Neisseria gonorrheae, Moraxella, typeable or nontypeable Haemophilus, Haemophilus nontypeable, Pseudomonas, Salmonella, Shigella, Enterobacter, Citrobacter, Klebsiella, E. coli, Clostridia, Bacteroides, Chlamydiaceae, Mycoplasma, Legionella, Treponemes, Borrelia, Candida or other yeast or other fungi, Plasmodium, Amoeba, herpes viruses, cytomegalovirus, Epstein-barr virus, varicella-zoster virus, influenza, adenoviruses, enteroviruses, or hemorrhagic viruses.

In another aspect of the invention, X is a truncated pneumococcal PsaA protein, pneumococcal serine/threonine protein kinase (StkP), pneumococcal serine/threonine protein kinase repeating unit (StkPR), pneumococcal PcsB protein, Mycobacterium tuberculosis mtb protein ESAT-6, M. tuberculosis cell wall core antigen, Chlamydia CT144, CT242 or CT812 polypeptides or fragments of these, Chlamydia DNA gyrase subunit B, Chlamydia sulfite synthesis/biphosphate phosphatase, Chlamydia cell division protein FtsY, Chlamydia methionyl-tRNA synthetase, Chlamydia DNA helicase (uvrD), Chlamydia ATP synthase subunit I (atpI), or Chlamydia metal dependent hydrolase.

In another embodiment of the present invention, X is a cancer antigen. In another embodiment of the invention, PS is a cancer antigen.

A particular embodiment of the present invention provides for an immunogenic composition comprising a fusion protein of a truncated pneumococcal PsaA protein and a nonhemolytic pneumolysin PdT protein, conjugated to a pneumococcal cell wall polysaccharide (CWPS).

Another embodiment of the present invention provides for a method of conferring TLR4-dependent protection against pneumococcal colonization comprising administering a composition comprising PsaA:PdT-PS or PsaA:PdT-CWPS.

Yet another embodiment prevides for a composition consisting essentially of a fusion protein (PsaA:PdT) containing truncated PsaA and a nonhemolytic variant of pneumolysin (PdT) conjugated with CWPS.

DESCRIPTION OF THE DRAWINGS

FIG. 1A provides a diagrammatic description of a truncated PsaA (22-309) and a nonhemolytic variant of pneumolysin (PdT) (W433F, D385N, and C428G) connected together by a polylinker GSGGGGS (SEQ ID NO:1). Protein was cloned into pQE30 plasmid and then transformed E. coli for expression. Proteins were expressed in E. coli by IPTG induction and then purified using Ni-NTA beads. FIG. 1B shows a SDS-PAGE characterization of the components. Lane 1, PdT; Lane 2, PsaA; Lane 3, PsaA:PdT.

(FIG. 3C): The mice were challenged intranasally with the serotype 6B strain four weeks post-immunization, and the density of colonization was determined seven days later by plating dilutions of nasal washes. No protection against colonization was observed in any of the immunization groups. Panels 3D and 3E: Mice were immunized with CT with or without the addition of a conjugate of PsaA (5 μg per dose) and CWPS (10 μg per dose). Immunization with PsaA-CWPS resulted in significantly higher anti-PsaA antibodies than in control mice (FIG. 3D), but no protection was observed following intranasal challenge (FIG. 3E). For all panels, horizontal lines represent geometric means and statistical analysis was performed using the Kruskal-Wallis test with Dunn's correction or Mann-Whitney U. *$P<0.05$; **$P<0.01$.

FIG. 5A shows C3H/HeOuJ (wild type) and C3H/HeJ (TLR4 defective) mice immunized twice intranasally with CT or the fusion conjugate with CT then challenged with strain 0603. In contrast to HeOuJ mice (wild-type) that were well protected against colonization following immunization with the fusion conjugate, HeJ mice (TLR4-defective) were not protected. FIG. 5B shows splenocytes from fusion conjugate-immunized HeOuJ and HeJ mice that were stimulated with the antigens as shown, and the IL-17A concentration in the cell supernatant measured after three days. Splenocytes from HeOuJ mice made significantly more IL-17A in response to WCA and PdT than splenocytes from HeJ mice.

FIG. 7A: Three weeks post-immunization, IL-17A production in vitro was assayed in blood samples incubated 6 days with pneumococcal whole-cell antigen. ***$P<0.0001$ determined by Mann-Whitney U test. FIG. 7B: Four weeks post-immunization the animals were challenged intranasally with TIGR4 strain expressing serotype 19F or serotype 6B strain 0603 and nasopharyngeal colonization was determined as described as in FIG. 3. Four mice were given IP injections of anti-CD4 antibodies just before challenge. Horizontal lines denote the geometric mean.

FIG. 11 shows T-cell responses following the immunization scheme and groups of FIG. 10. Two weeks after second and third immunization, whole blood of mice was sampled and stimulated as indicated to measure T cell cytokine (IL-17A and IFNγ) responses. Mean and SEM are shown, N=10 mice per group.

DETAILED DESCRIPTION

Figure 1:
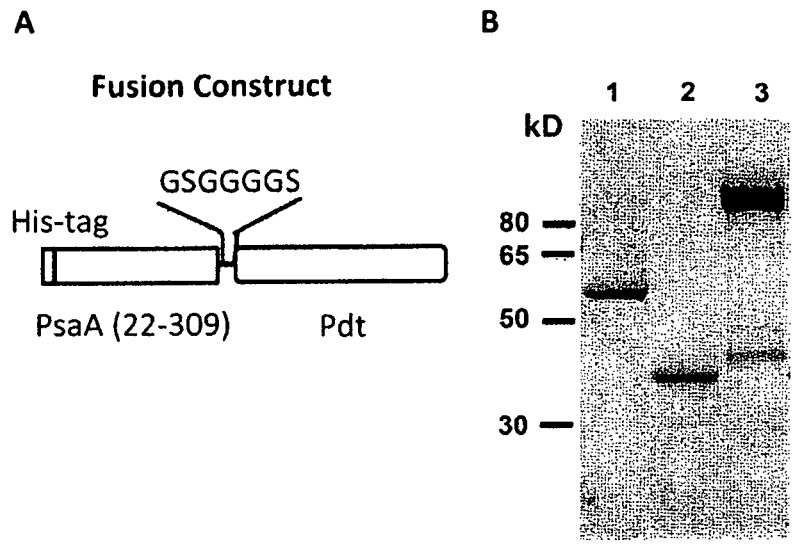
FIGS. 1A and 1B depict construction of a PsaA:PdT fusion protein.

The invention presented herein is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. "Immunogenic" means a substance is capable of inducing an immune response in a subject. Although any known methods, devices, and materials may be used in the practice or testing of the invention, the methods, devices, and materials in this regard are described herein.

The present invention provides for enhanced immunogenicity of a composition consisting of a polysaccharide (e.g., dextran, CWPS) conjugated to pneumolysoid fused with a target protein that results in greatly enhanced immunity to the target protein and offers the possibility of providing protection against other pathogens. One embodiment provides for conjugate vaccine in which a fusion protein of PsaA and PdT was coupled to CWPS. This conjugate was evaluated with respect to preservation of TLR4 activity and to immunogenicity. Serum antibodies, priming for IL-17A production and protection against nasopharyngeal colonization, in response to both intranasal (i.n.) and subcutaneous (s.c.) vaccination, were assayed, and the s.c. route was examined further in a fatal aspiration pneumonia model. The fusion conjugate was significantly more protective than a mixture of its components or than any of the three combinations of two antigens. The fusion conjugate, when administered i.n., reduced nasopharyngeal colonization by a strain of serotype 6B, a major disease type in infancy. Although the conjugate elicited antibodies to all three of its component antigens, the protection against colonization appears more to depend upon priming for enhanced elicitation of IL-17A upon encounter with pneumococci. Lu et al., 77 Infect. Immun. 2076-83 (2009).

The present invention provides for the design of immunogenic conjugates or vaccines against many pathogens for which generating either antibody and/or cellular immunity is desirable. Over the past few years, there has been a growing list of pathogens for which the combination of the two forms of immune responses has been shown to play a role in defense against the pathogen. This is true for pneumococcus, *Staphylococcus aureus*, herpes viruses, *Chlamydia trachomatis*, to name a few. Thus, the immunogenic conjugate of the present invention could be used to stimulate immunities to bacterial (including mycobacterial), fungal, parasitic, and viral pathogens.

Regarding bacterial pathogens, the antigenic X component of the present synergistic, immunogenic fusion conjugates may be derived from Staphylococci species, Streptococci species (including Group A and B), Enterococci species; *Listeria, Bacillus* (including anthrax), *Corynebacteria, Neisseria* (meningitidis and gonorrheae), *Moraxella, Haemophilus* (typeable and nontypeable), *Pseudomonas* (*aeruginosa* and others), *Salmonella* (*typhi* and nontyphi), *Shigella*, resistant gram-negative enteric bacteria (*Enterobacter, Citrobacter, Klebsiella, E. coli*, etc.), *Clostridium difficile* and other *Clostridia, Bacteroides* and other anaerobes, Chlamydiaceae species (*C. trachomatis* and *C. pneumoniae*), *Mycoplasma* and *Legionella* as well as the *Treponemes* (*syphilis, leptospirosis*) and *Borrelia*.

Figure 9:
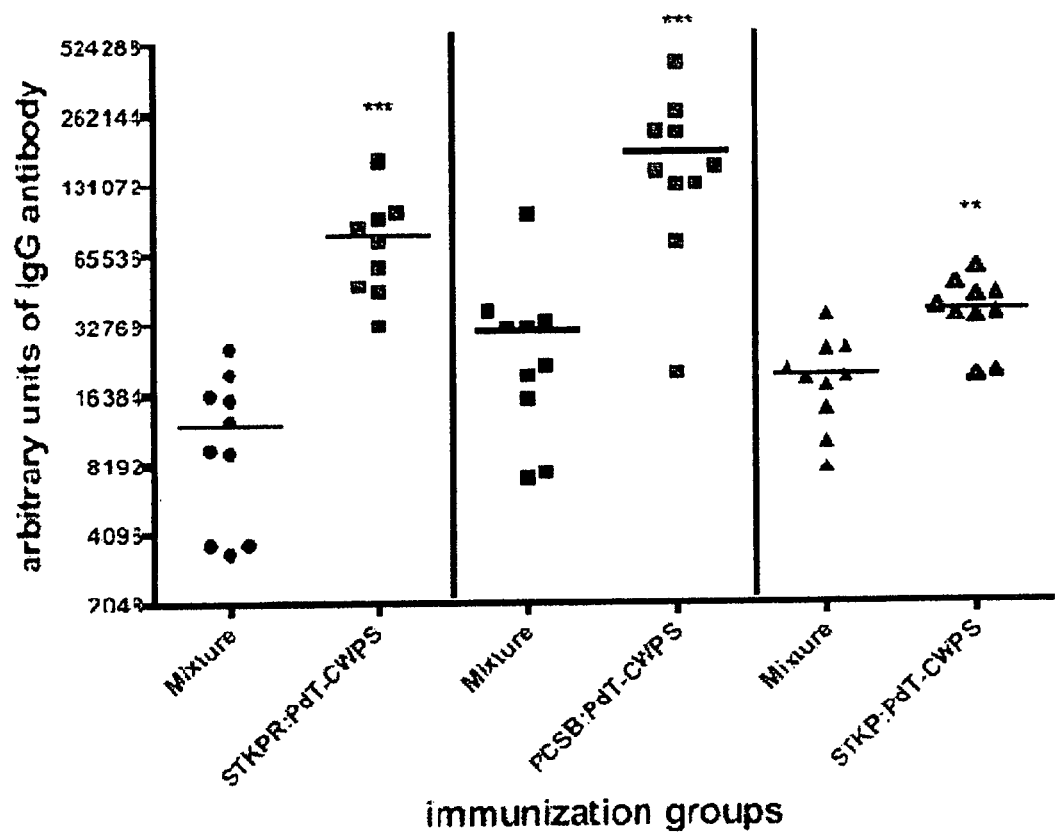
FIG. 9 shows the IgG antibody response in s.c. immunization groups to mixtures of X, PdT and CWPS antigens, compared with X:PdT-CWPS conjugates of the same antigens, where X represents either StkpR, PcsB, or Stkp. *$P<0.0005$; $P<0.01$.

Thus, in a particular embodiment of the present invention, PdT was genetically fused to pneumococcal PcsB protein (derived from pcsB, which encodes the protein required for cell separation in group B streptococci) (Giefing et al., 205 J. Exp. Med. 117-31 (2007)), and conjugated to CWPS. This conjugate elicited more IgG against PcsB than did the corresponding mixture of antigens. In another particular embodiment, PdT was genetically fused to the pneumococcal serine/threonine protein kinase (StkP) (Giefing et al., 2007), and conjugated to CWPS. This conjugate elicited more IgG against StkP than did the corresponding mixture of antigens. The same synergistic response was observed in another antipneumococcal preparation in which pneumococcal serine/threonine protein kinase repeating unit, StkPR, was genetically fused to PdT and conjugated to CWPS (FIG. 9).

Another class of bacteria for which the antigenic X component of the present synergistic, immunogenic fusion conjugates may be derived include *Mycobacteria*, especially *Mycobacterium tuberculosis*—thus for example the X is a protein from tuberculosis, such as mtb protein ESAT-6, for example or cell wall core antigen (Kaplan et al., 5 P.N.A.S. USA 1917-21 (1988)) or a protein from *M. leprae*, e.g., PP-I (Chirmule et al., 86 Int'l Arch. Allergy Appl. Immun. 19-27 (1988))

As noted above, *Chlamydia* species may provide the target X antigen in the present invention. Chlamydiaceae (consisting of Chlamydiae and Chlamydophila), are obligate intracellular gram-negative bacteria. *Chlamydia trachomatis* infections are among the most prevalent bacterial sexually transmitted infections, and perhaps 89 million new cases of genital chlamydial infection occur each year. The *Chlamydia* of the present invention include, for example, *C. trachomatis, Chlamydophila pneumoniae, C. muridarum, C. suis, Chlamydophila abortus, Chlamydophila psittaci, Chlamydophila caviae, Chlamydophila fells, Chlamydophila pecorum,* and *C. pneumoniae*. Animal models of chlamydial infection have established that T-cells play a critical role both in the clearance of the initial infection and in protection from reinfection of susceptible hosts. Hence, the conjugates of the present invention may provide particular value by eliciting cellular immune responses against chlamydial infection.

More specifically, Chyamidial antigens useful in the present invention include DNA gyrase subunit B, sulfite synthesis/biphosphate phosphatase, cell division protein FtsY, methionyl-tRNA synthetase, DNA helicase (uvrD); ATP synthase subunit I (atpI) or a metal-dependent hydrolase (U.S. Patent Application Pub. No. 20090028891). Additional *Chlamyidia trachomatis* antigens include CT144 polypeptide (SEQ ID NO:7), a peptide having amino acid residues 67-86 of CT144 (SEQ ID NO:8), a peptide having amino acid residues 77-96 of CT144 (SEQ ID NO:9), CT242 protein (SEQ ID NO:10), a peptide having amino acids 109-117 of CT242 (SEQ ID NO:11), a peptide having amino acids 112-120 of CT242 polypeptide (SEQ ID NO:12), CT812 protein (from the pmpD gene) (SEQ ID NO:13), a peptide having amino acid residues 103-111 (SEQ ID NO:14) of the CT812 protein; and several other antigenic peptides from *C. trachomatis*: NVTQDLTSSTAKLECTQDLI (SEQ ID NO:15), AKLECTQDLIAQGKLIVTNP (SEQ ID NO:16), SNLKRMQKI (SEQ ID NO:17), AALYSTEDL (SEQ ID NO:18), FQEKDADTL (SEQ ID NO:19), QSVNELVYV (SEQ ID NO:20), LEFASCSSL (SEQ ID NO:21), SQAE-GQYRL (SEQ ID NO:22), GQSVNELVY (SEQ ID NO:23), and QAVLLLDQI (SEQ ID NO:24) (WO 2009/020553). Additionally, *Chlamydia pneumoniae* antigens including homologues of the foregoing polypeptides (see U.S. Pat. No. 6,919,187), may be used as X in the X:PdT-PS constructs of the present invention.

Fungal targets of the present synergistic, immunogenic conjugates include *Candida* species and other yeast; or other fungi (aspergillus, other environmental fungi). Regarding other parasites, malaria as well as worms and amoebae may provide the antigenic X for the synergistic, immunogenic conjugates of the invention.

Viral targets for the present synergistic, immunogenic conjugates include, in particular, herpes viruses including herpes simplex viruses, cytomegalovirus, Epstein-Barr virus, and varicella-zoster virus. Other common viral causes of disease in humans and animals may also be targeted, including influenza, adenoviruses, enteroviruses, and hemorrhagic viruses.

The X:PdT-PS conjugate may also be constructed to provide for a synergistic immunogenic reaction to an antigenic sugar moiety. For example, the Vi polysaccharide of *Salmonella typhi* could be used. Vi capsular polysaccharide has been developed against bacterial enteric infections, such as typhoid fever (Robbins et al., 150(3) J. Infect. Dis. 436-49 (1984); Levine et al., 7 Baillieres Clin. Gastroenterol. 501-17 (1993)). Vi is a polymer of α-1→4-galacturonic acid with an N-acetyl at position C-2 and variable O-acetylation at C-3. The virulence of *S. typhi* correlates with the expression of this molecule (Sharma et al., 101 P.N.A.S. USA 17492-97 (2004)). The Vi polysaccharide vaccine of *S. typhi* has several advantages: Side effects are infrequent and mild, a single dose yields consistent immunogenicity and efficacy. Vi polysaccharide may be reliably standardized by physicochemical methods verified for other polysaccharide vaccines, Vi is stable at room temperature and it may be administered simultaneously with other vaccines without affecting immunogenicity and tolerability (Azze et al., 21 Vaccine 2758-60 (2003)).

Thus, the Vi polysaccharide of *Salmonella typhi* may be conjugated to a fusion protein where the X is from the same or from another organism, such that the resulting vaccine confers immunity against one pathogen, or two different pathogens: if X confers protection against pneumococcus, a Vi-X: PdT construct raises an immunogenic response against *S. typhi* and pneumococcus. Other examples include combining sugars from encapsulated bacteria (such as meningococcus, *S. aureus*, pneumococcus, etc.) and tuberculous protein, to provide a vaccine that protects against two different pathogens.

Other polysaccharide (PS) moities that may be used in the present invention in alternative to dextran, CWPS, etc., include carbohydrate antigens of cancers. For example, the Tn antigen, an oligosaccharide expressed exclusively by cancer cells (Buskas et al., 44 Angew Chem. Int'l Ed. 5985-88 (2005)).

In one aspect of the invention, the PS has a molecular mass of <500 kDa. In another aspect of the invention, the PS has a molecular mass of <70 kDa.

Additionally, the present invention also provides for synergistic, immunogenic conjugates against cancer. In these conjugates, the target X protein is a protein expressed predominantly on the cancer cells, such that the conjugate elicits both potent humoral and potent cellular immunity to this protein. A large number of cancer-associated antigens have been identified, several of which are now being used to make experimental cancer treatment vaccines and are thus suitable for use in the present embodiments. Antigens associated with more than one type of cancer include Carcinoembryonic antigen (CEA); Cancer/testis antigens, such as NY-ESO-1; Mucin-1 (MUC1) such as Sialyl Tn (STn); Gangliosides, such as GM3 and GD2; p53 protein; and HER2/neu protein (also known as ERBB2). Antigens unique to a specific type of cancer include a mutant form of the epidermal growth factor receptor, called EGFRvIII; Melanocyte/melanoma differentiation antigens, such as tyrosinase, MART1, gp100, the lineage related cancer-testis group (MAGE) and tyrosinase-related antigens; Prostate-specific antigen; Leukaemia-associated antigens (LAAs), such as the fusion protein BCR-ABL, Wilms' tumour protein and proteinase 3; and Idiotype (Id) antibodies. See, e.g., Mitchell, 3 Curr. Opin. Investig. Drugs 150-58 (2002); Dao & Scheinberg, 21 Best Pract. Res. Clin. Haematol. 391-404 (2008).

Another approach in generating an immune response against cancer employs antigens from microbes that cause or contribute to the development of cancer. These vaccines have been used against cancers including hepatocellular carcinoma (hepatitis B virus, hepatitis C virus, *Opisthorchis viverrin*), lymphoma and nasoparyngeal carcinoma (Epstei-Barr virus), colorectal cancer, stomach cancer (*Helicobacter pylori*), bladder cancer (*Schisosoma hematobium*), T-cell leukemia (human T-cell lymphtropic virus), cervical cancer (human papillomavirus), and others. To date, there have been clinical trials for vaccines targeting Bladder Cancer, Brain Tumors, Breast Cancer, Cervical Cancer, Kidney Cancer, Melanoma, Multiple Myeloma, Leukemia, Lung Cancer, Pancreatic Cancer, Prostate Cancer, and Solid Tumors. See Pardoll et al., ABELOFF'S CLIN. ONCOL. (4th ed., Churchill Livingstone, Philadelphia 2008); Sioud, 360 Methods Mel. Bio. 277-318 (2007); Pazdur et al., 30(3) J. Infusion Nursing 30(3):173-78 (2007); Parmiani et al., 178 J. Immunol. 1975-79 (2007); Lollini et al., 24 Trends Immunol. 62-66 (2003); Schlom et al., 13 Clin. Cancer Res. 3776-82 (2007); Banchereau et al., 392 Nature 245-52 (1998); Finn, 358 New Engl. J. Med. 2704-15 (2008); Curigliano et al., 7 Exp. Rev. Anticancer Ther. 1225-41 (2007). Thus, the present embodiments encompass both preventive/prophylactic cancer vaccines and treatment/therapeutic cancer vaccines.

Recombinant proteins may be conveniently expressed and purified by a person skilled in the art using commercially available kits, for example PROBOND™ Purification System (Invitrogen Corp., Carlsbad, Calif.). Alternatively, standard molecular biology protocols may be used, as for example described in Sambrook, et al., MOL. CLONING. A LAB. MANUAL (Cold Spring Harbor Press, 1989); CURRENT PROTOCOLS MOL. BIO. (Ausubel et al., eds., John Wiley & Sons, Inc. 1995-1999); and CURRENT PROTOCOLS PROT. SCI. (Coligan et al., eds., John Wiley & Sons, Inc. 1995-1999).

Specific embodiments of the present invention provide for synergistic, immunogenic conjugates which are capable of eliciting an immune response in an animal. More specifically, the compositions elicit both humoral and cellular immunity, and in many instance mucosal immunity. Embodiments of the present invention provide at least partial protection from or partial improvement after infection by, in particular, pneumococcal infection. Pneumococci cause a number of diseases, such as meningitis, pneumonia, bacteraemia, and otitis media. Almost one million children die of pneumococcal diseases worldwide every year. *S. pneumoniae* have been studied extensively, and at least some of the genomes sequenced (see, e.g., U.S. Pat. No. 7,141,418). Antibodies to the capsular polysaccharides, which define the known serotypes, confer serotype-specific protection, and have been called the only significant mechanism of acquired immunity (Janeway et al., IMMUNOLOGY (Garland Pub., NY, 2001)). The application of protein-polysaccharide conjugate vaccine, PCV7, has reduced diseases significantly (Black et al., 24(S2) Vaccine 79-80 (2006); Hansen et al., 25(9) Pediatr. Infect. Dis. J. 779-81 (2006)). Yet, recent studies have shown that the lack of other serotypes in PCV7 has resulted in emerging replacement pneumococcal serotypes (Pichichero & Casey, 26(S10) Pediatr. Infect. Dis. J. S12-16 (2007)).

Certain pneumococcal antigens common to all serotypes of the species have been shown to have immunoprotective potential despite the encapsulation, e.g., the surface proteins PspA, PspC, PsaA and the cytotoxin pneumolysin or pneumolysoid mutants (Basset et al., 75 Infect. Immun. 5460-64 (2007); Briles et al., 18 Vaccine 1707-11 (2000)); the use of genomics and mutational libraries has identified several dozen additional species-common proteins (Hava Camilli, 45 Mal. Microbial. 1389-1406 (2002); Wizemann et al., 60 Infect. Immun. 1593-98 (2001)). Immunity has been induced by individual antigens in animal models (Alexander et al., 62 Infect. Immun. 5683-88 (1994); Balachandran et al., 70 Infect. Immun. 2526-34 (2002); Chung et al., 33 170 J. Immunol. 1958-63 (2003); Glover et al., 76 Infect. Immun. 2767-76 (2008); Wu et al., 175 J. Infect. Dis. 839-46 (1997)), but no vaccine based on a common antigen has been approved for human use to date.

One disadvantage of any strategy relying on single proteins is that, given the genetic diversity of pneumococci as well as its propensity for genetic transformation, it may be evaded. Further, antibody of a single common specificity may not bind to the capsulated cell in sufficient multiplicity to be effective. For this reason, vaccination with mixtures of species antigens has been proposed; in some studies, synergistic effects of mixtures of three proteins in systemic vaccination were demonstrated (Ogunniyi et al., 68 Infect. Immun. 3028-33 (2000)). Recently, it was shown that a mixture of three species-common proteins administered intranasally (i.n.) with cholera toxin adjuvant confers protection against colonization in an antibody-independent, CD4+ (and likely IL-17A)-dependent manner (Basset et al., 2007).

The present invention provides for a covalent combination of three species antigens: a non-toxic derivative of pneumolysin, PdT (Asp385Asn, Cys428Gly and Trp433Phe), the surface adhesin protein A (PsaA), coupled to cell wall polysaccharide (CWPS) (molecular weight about 26,400; Koenig & Perrings, 1 J. Biophys. Biochem. Cytol 93 (1955)). Surprisingly, the conjugate protected mice against colonization in a synergistic fashion, whereas mice immunized with a mixture of the antigens were not so protected. Additionally, in contrast to wild-type C3H/HeOuJ mice, TLR4-deficient C3H/HeJ mice were not protected by the intranasal immunization with conjugate, implying that TLR4 plays a role in protection. Indeed, subcutaneous immunization with the protein fusion conjugate resulted in a 90% reduction in pneumococcal colonization density, and also fully protected mice from lethal lung inhalation challenge by highly virulent serotype 3 strain.

Additionally, mice immunized intranasally with pneumococcal CWPS plus a mucosal adjuvant became resistant to nasopharyngeal colonization, and the immunity is antibody-independent and dependent upon CD4+ T-cells. Protection against colonization in mice is mediated by $T_H17$ cells, and correlated with IL-17A expression by blood samples stimulated with pneumococcal antigens in vitro. In a mouse aspiration pneumonia model, CWPS also provides protection against invasive disease. In order to enhance immune response to CWPS, conjugation of CWPS to pneumococcal protein carriers was generated with the goal to enhance immune response to both CWPS and pneumococcal proteins. It was shown recently that this IL-17 promotes agar surface killing of pneumococci by polymorphonuclear leukocytes in the absence of antibody and complement, and a similar mechanism might operate at the nasopharyngeal mucosa (Lu et al., 4(9) PLoS Pathog. e1000159 (Sep. 19, 2008)).

Intranasal immunization using enterotoxin or related adjuvants such as CT, although immunologically advantageous, has raised safety concerns due to possible entry into the central nervous system via the olfactory nerve, and also due to evidence following the use of a killed nasal influenza vaccine in Switzerland (Mutsch et al., 350 N. Engl J. Med. 896-903 (2004)). Thus, subcutaneous presentation with alum—the standard adjuvant in human vaccination—was tested. By this mode of immunization, the fusion conjugate was active in antibody induction and priming for IL-17A, and it reduced nasopharyngeal colonization by the two tested serotypes, 19F and 6B. Protection was abrogated by administration of neutralizing antibodies to CD4+ T cells, suggesting dependence on IL-17A and non-dependence on the antibody responses. The antibody responses to the conjugate, however, would be highly advantageous in immunization strategy; if pneumococci evaded the T-cell-mediated protection against colonization, the antibodies would represent an additional line of defense.

Protection by s.c. administration was tested also in a model of fatal disease due to aspiration of a highly capsulated serotype 3 strain. Here, the fusion conjugate, but not the mixture of its three component antigens, was completely protective, again demonstrating synergy of the fusion conjugate. There was enhancement from coupling to CWPS, seen with the IL-17A priming, which may be a physicochemical effect or due specifically to the potential of zwitterionic polysaccharides to activate $T_H17$ cells (Briles et al., 153 J. Exp. Med. 694-705 (1981); Chung et al., 170 J. Immunol. 1958-63 (2003); Cobb et al., 117 Cell 677-87 (2004); Kalka-Moll et al., 169 J. Immunol. 6149-53 (2002); Malley et al., 74 Infect. Immun. 2187-95 (2006); Tzianabos et al., 275 J. Biol. Chem. 6733-40 (2000)). The synergy of the conjugate may also depend, in part, upon the TLR4 stimulatory property of the PdT component, which was preserved in the present conjugate. Chemical linkage to PdT gave enhanced responses to PsaA and CWPS individually as well as in the fusion conjugate. This result agrees with the concept that the presence of TLR agonist and antigen on the same particle enhances processing for immunity (Blander & Medzhitov, 440 Nature 808-12 (2006)).

These results are generalizable to other proteins (beyond PsaA and involving pathogens other than pneumococci). Thus, a construct consisting of CWPS conjugated to pneumolysoid fused with a protein target results in greatly enhanced immunity to the target protein and offers the possibility of providing protection against other pathogens.

Further, regarding the particular embodiments of presented herein, pneumococcal cell wall polysaccharide (CWPS), a ribitol teichoic acid linked to the muramic residues of the cell wall peptidoglycan, and the membrane-bound lipoteichoic acid (LTA) (consisting of the identical teichoic acid with a glycolipid end group), has been identified as a species antigen. CWPS, and compositions including preparations of the polymer or its components, have been tested as a vaccine in animal models (Briles et al., 153(3) J. Exp. Med. 694-705 (1981); Szu et al., 39(2) Infect. Immun. 993-99 (1983); Wallick et al., 130(6) J. Immunol. 2871-75 (1983); Szu et al., 54(2) Infect. Immun. 448-55 (1986); Skov et al., 56(3) Infect. Immun. 1890-96 (1988)). Serum antibodies to phosphorylcholine protect mice against parenteral challenge with capsulated serotype 3 pneumococci (Briles et al., 153(3) J. Exp. Med. 694-705 (1992)).

Additionally, compositions including phosphorylcholine conjugated to a carrier protein and mixed with Freund's adjuvant protected mice against an intravenous challenge with serotype 1 or serotype 3 pneumococci (Wallick et al., 1983). Subsequent studies, however, failed to show protection in parenterally challenged mice by antibodies to phosphorylcholine or to determinants within the polymer "backbone" (Szu et al., 1986; Nielsen et al., 14(4) Microbial Pathogenesis, 299-305 (1993)). Studies in humans also failed to show any association between antibodies to phosphorylcholine and protection against invasive or mucosal pneumococcal disease (Musher et al., 161(4) Infect. Dis. 736-40 (1990); Koskela et al., 30(6) J. Clin. Microbial. 1485-90 (1992)).

The issue was revisited recently to evaluate whether the initial successes established by Briles et al. could be reproduced using different models and routes of immunization. Intranasal immunization with CWPS confers significant and long-lasting protection against nasopharyngeal pneumococcal colonization and aspiration pneumonia leading to sepsis (Malley et al., 74(4) Infect. Immun. 2187-95 (2006)). Treatment of CWPS with periodate, which destroys the PS component, eliminates immunogenicity and protection, suggesting that the PS is a critical component of protection. The dose of CWPS required, however, is quite high: 100 µg per dose (given twice i.n.) is required for protection against colonization.

Protection against colonization is antibody-independent, CD4+ T-cell-dependent and IL-17A dependent: antibodies to IL-17A abrogate protection (Malley et al., 2006) and mice lacking IL-17A receptor are not protected by immunization with CWPS. This MHC class II-dependent protection elicited by a PS is consistent with recent data showing that a PS with a zwitterionic charge motif within the repeating unit (such as CWPS) could activate CD4+ T cells in a process that is dependent on MHC class II (Tzianabos et al., 275(10) J. Biol. Chem. 6733-40 (2000); Cobb et al., 117(5) Cell 677-87 (2004)). It is believed that these PS (including PS A and PS B of *Bacteroides fragilis*, and the CWPS of pneumococci) are oxidized by nitric oxide and processed via MHC II by B-cells to T-cells through interactions with T-cell receptors.

Pneumolysin, the cholesterol-dependent cytolysin, is 53 kDa protein composed of 470 amino acids and is encoded by the pneumolysin (ply) gene. Pneumolysin belongs to a family of protein toxins known as the 'thiol-activated cytolysins' and is a common component of almost every *S. pneumoniae* isolate. A non-toxic derivative PdT (Asp385Asn, Cys428Gly, Trp433Phe) activates cells via TLR4 (Malley et al., 100(4) P.N.A.S. USA, 1966-67 (2003); Srivastava et al., 73(10) Infect. Immun. 6479-87 (2005)). It has also been suggested that immunization with an antigen and TLR agonists is significantly more effective when the TLR agonist is part of the antigenic cargo (Blander & Medzhitov, 440(7085) Nature 808-12 (2006)), rather than just added in solution with the antigen. The IL-17A pathway is also known to be dependent on TLR involvement (Kolls & Linden, 21(4) Immunity, 467-76 (2004)).

Pneumococcal surface adhesin protein A (PsaA) is good candidate for vaccine development because studies have shown that PsaA exists in ninety pneumococcal serotypes, including clinically relevant strains (Morrison et al., 38(1) J. Clin. Microbial. 434-37 (2000)), and immunization with PsaA protected mice from both nasal colonization and lethal infection (Talkington et al., 21(1) Microb. Patho. 17-22 (1996); Oliveira et al., 8(4) Microbes Infect. 1016-24 (2006)). A mixture of three proteins (pneumococcal surface antigen C [PspC], PsaA, and PdT), administered i.n. with adjuvant, confers protection against colonization, also in an antibody-independent, CD4+ (and likely IL-17A)-dependent manner (Basset et al., 75(11) Infect. Immun. 5460-64 (2007)).

A particular nonhemolytic variant of pneumolysin (PdT) (W433F, D385N, and C428G) and PsaA were chosen as the fusion protein carrier because PdT is a TLR4 ligand and PsaA has been shown to provide protection from pneumococcal colonization. Purified PdT and PsaA were conjugated to CWPS by 1-Cyano-4-dimethylaminopyridinium tetrafluoroborate (CDAP) using the method described previously (Lees et al., 14(3) Vaccine. 190-98 (1996)), and then run through a Sepharose S300 column. Fractions from void volume were collected and filter sterilized. Analysis of the conjugate revealed that it contains a CWPS:protein ratio of 5:4 for PdT-CWPS and 2:1 for PsaA-CWPS.

Figure 2:
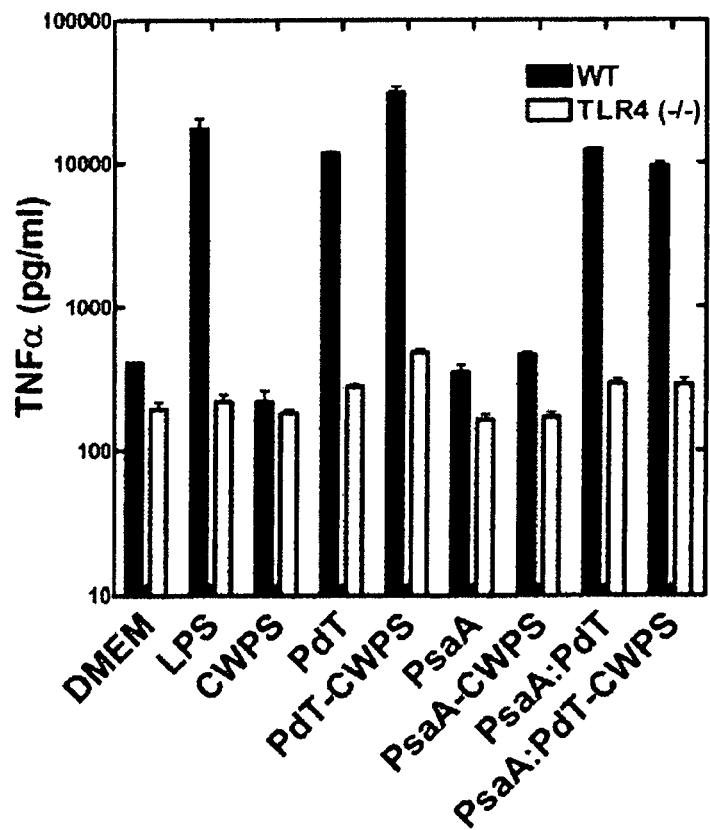
FIG. 2 shows the retention of TLR4 stimulatory activity of PdT in the conjugate and fusion constructs. Immortalized macrophage cell lines (WT or TLR4−/−) were stimulated with 36 nM of each stimulus for 20 hours and the concentration of TNF-α in cell supernatant was measured by ELISA.

PdT is a TLR4 agonist, and TLR4 signaling is important for protecting mice following intranasal challenge with pneumolysin-positive encapsulated pneumococci (Malley et al., 100 P.N.A.S. USA 1966-71 (2003)). Therefore the fusion protein and PdT conjugates were tested for retention of TLR4 activity: wild-type or TLR-knockout macrophages were incubated in vitro with the various antigens for twenty hours, and the production of TNF-α, was measured by ELISA (FIG. 2). As expected, neither PsaA nor CWPS induced a TNF-α response, while the lipopolysaccharide (LPS) used as a positive control produced a two-log increase in TNF-α secretion in the TLR4+ cells. PdT, PdT:PsaA fusion protein, and the two PdT-containing CWPS conjugates induced similar TLR4-dependent responses. To exclude that the stimulation was due to LPS contamination of the recombinant proteins, the samples were tested after boiling for 1 hour. Boiling did not affect activity of the control LPS, while TNF-α production was eliminated in all other samples. Thus the TLR4-dependent response was not due to LPS contamination; furthermore, the fusion and coupling of PdT did not diminish its TLR agonist activity.

Figures 3A, 3B:
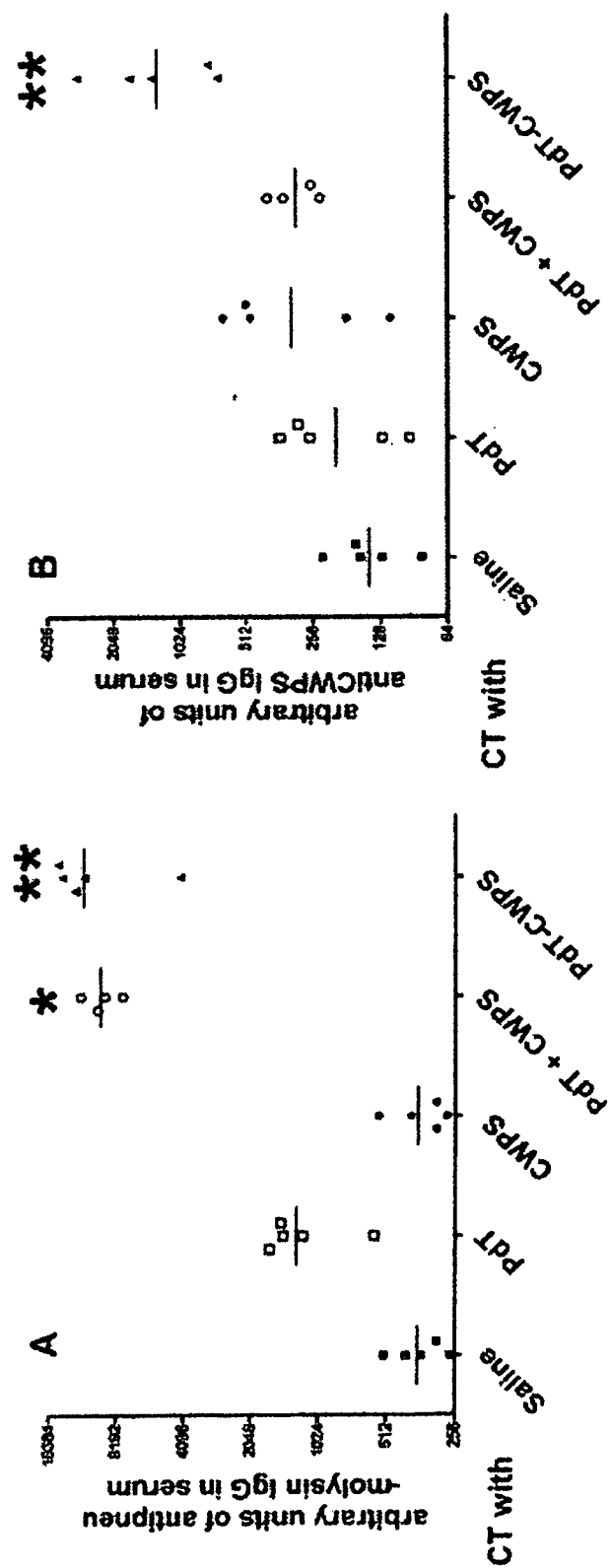
FIGS. 3A to 3E present responses to intranasal immunization with either two-component PdT-CWPS and PsaA- CWPS conjugates, or uncoupled antigens. Panels A-C: Mice were vaccinated weekly twice with 1 μg of cholera toxin (CT) as adjuvant. Antigen dosages, coupled or not, were 8 μg of PdT and 10 μg of CWPS. Blood was taken three weeks after the second immunization. Serum IgG antibody responses were assayed to PdT (FIG. 3A) and CWPS (FIG. 3B). Mice immunized with the PdT-CWPS conjugate made significantly more anti-PdT and anti-CWPS antibodies than mice that received CT alone, and more anti-CWPS antibodies than mice that received the mixture of PdT and CWPS.

Intranasal immunizations with two-component conjugates PdT-CWPS and PsaA-CWPS, or uncoupled controls, were compared. Mice were intranasally immunized, twice at one-week interval, with CWPS, PsaA, PdT, mixtures of CWPS and the proteins, or the conjugates PdT-CWPS or PsaA-CWPS, all with amounts of each antigen equalized; 1 µg of cholera toxin (CT) was used as adjuvant and was always tested alone as one control. The serum IgG antibody responses to PdT, CWPS, or PsaA measured by ELISA in sera taken three weeks after the last immunization are shown in FIG. 3: The anti-PdT responses in the PdT-CWPS conjugate immunized mice were also greater than the respective mixture (FIG. 3A). Anti-CWPS (FIG. 3B) and anti-PsaA (FIG. 3D) antibody responses in the PdT-CWPS or PsaA-CWPS conjugate immunized mice were greater than those in mice immunized with mixtures of the two antigens. The mice were challenged intranasally with serotype 6B pneumococcus strain 0603 four weeks after the second immunization.

Figure 3C:
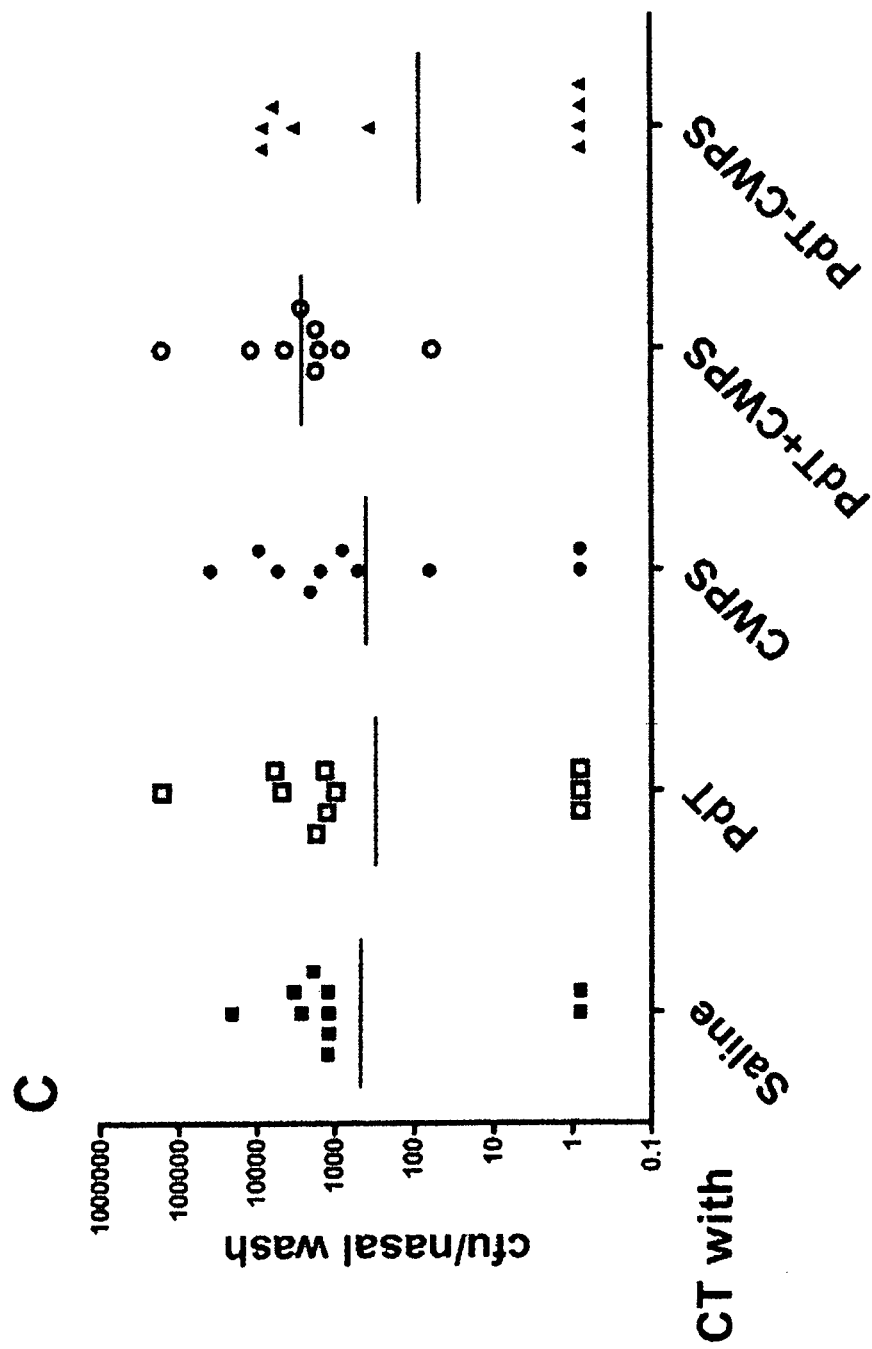
Figures 3D, 3E:
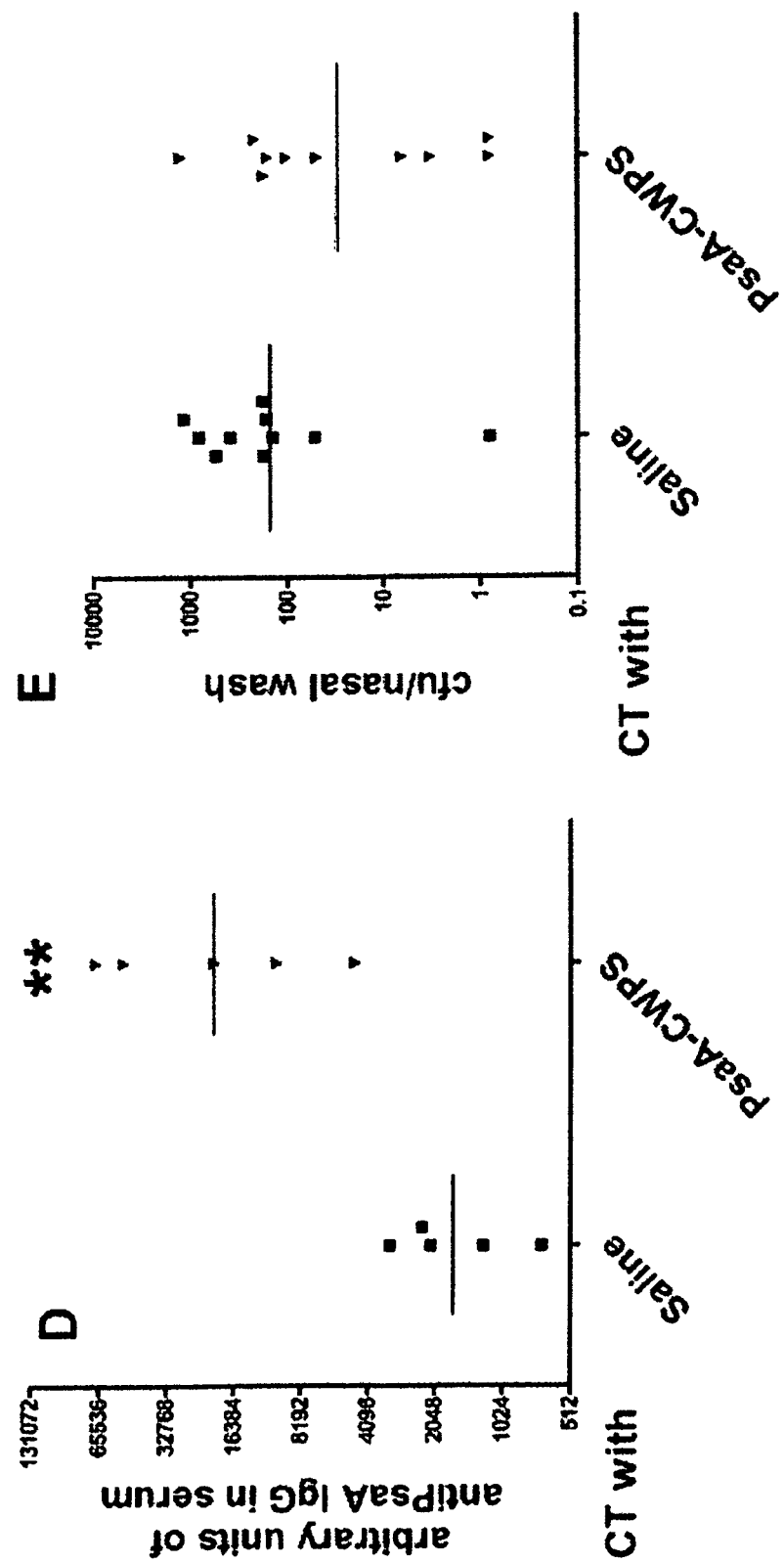

Colony-forming units (CFU) per mouse in nasal washes collected one week after challenge are shown in FIGS. 3C and 3E. No statistically significant reduction of bacterial colonization, compared to the controls receiving CT alone, was observed in any of the immunization groups.

Regarding the intranasal immunization with PsaA:PdT-CWPS, in order to enhance the protection, a fusion protein of PsaA and PdT with a poly-linker was constructed, as shown in FIG. 1A, and was generated and purified as described herein. PsaA:PdT was conjugated to CWPS by CDAP and purified by gel filtration (FIG. 1B). The ratio between protein and polysaccharide was determined to be 1/1.1.

Figures 4A, 4B:
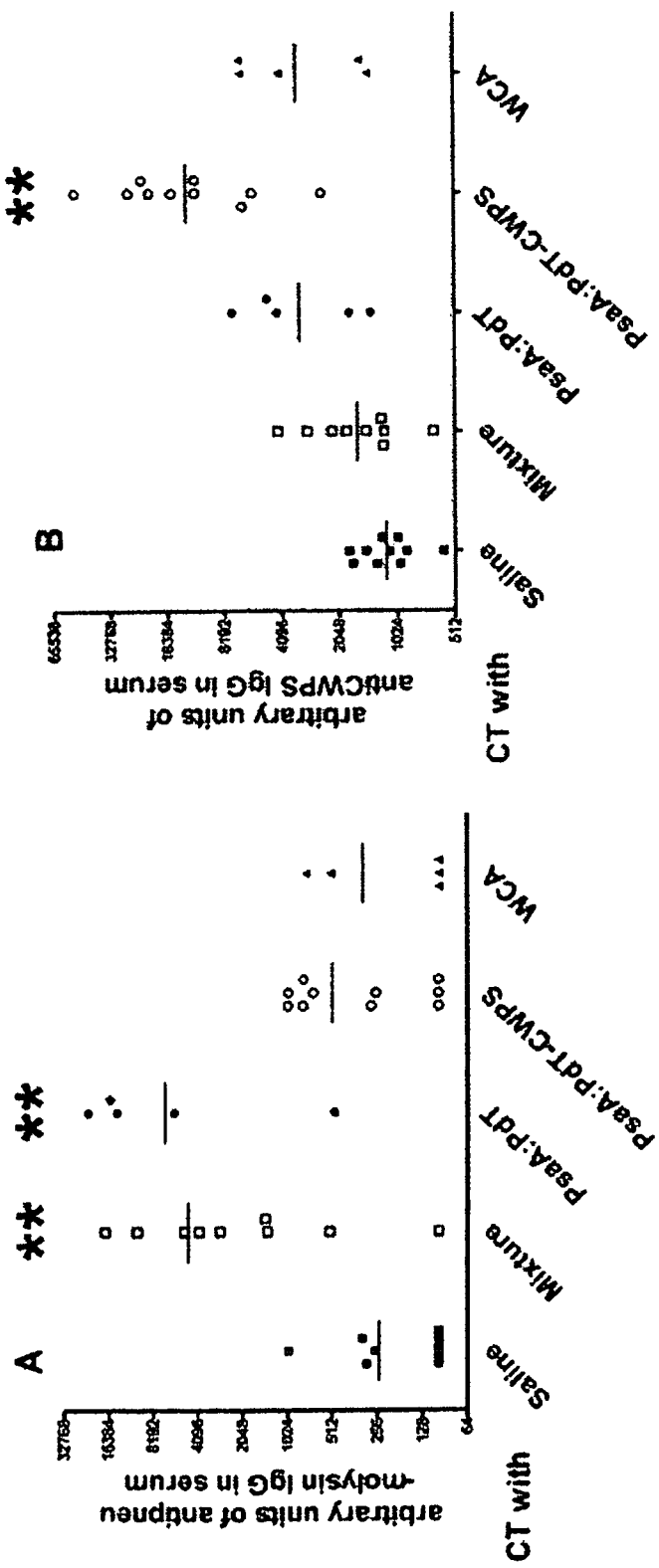
FIGS. 4A to 4E reflect responses to intranasal immunization with the PdT:PsaA-CWPS fusion conjugate or controls. Immunizations were as in FIG. 3. The conjugate contained 7.7 μg of PdT, 5 μg of PsaA, and 14 μg of CWPS. The control antigens included a mixture of the individual components in dosage equal to the conjugate, the PdT:PsaA fusion protein in equal protein dosage, and WCA, the pneumococcal whole-cell antigen, about $10^8$ cells=100 μg dry weight. Three weeks post-immunization, antibodies were measured against PdT (FIG. 4A), CWPS (FIG. 4B), and PsaA (FIG. 4C). IL-17A production in vitro was measured in blood samples incubated six days with pneumococcal whole-cell antigen (FIG. 4D). Four weeks post-immunization, the mice were challenged and nasopharyngeal colonization was determined as in FIG. 3E. For all panels, horizontal lines represent geometric means and statistical analysis was performed using the Kruskal-Wallis test with Dunn's correction or Mann-Whitney U. *$P<0.05$; $P<0.01$; *$P<0.001$.
Figures 4C, 4D:
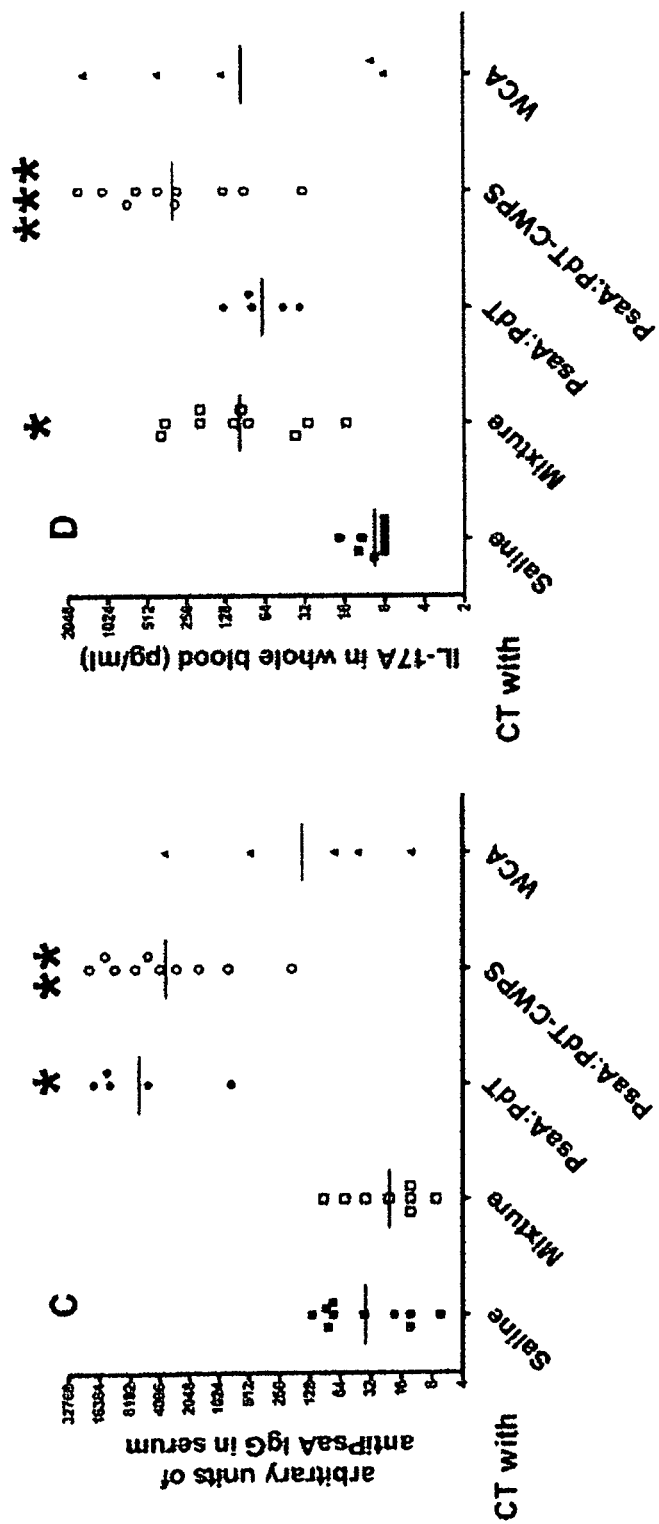

Mice were similarly immunized with the fusion conjugate. A mixture of the three antigens or the PsaA:PdT fusion protein alone (all given with the adjuvant CT) was used as control; also included as controls were mice vaccinated with the pneumococcal WCA and CT. IgG antibodies to PdT, CWPS, and PsaA at three weeks after immunization are shown in FIG. 4. The conjugate induced higher titers of anti-CWPS than the mixture (FIG. 4B); the conjugate and the fusion protein both induced higher titers of anti-PsaA than the mixture (FIG. 4C). Interestingly, however, the conjugate induced less anti-PdT IgG than the mixture or fusion protein (FIG. 4A).

Figure 4E:
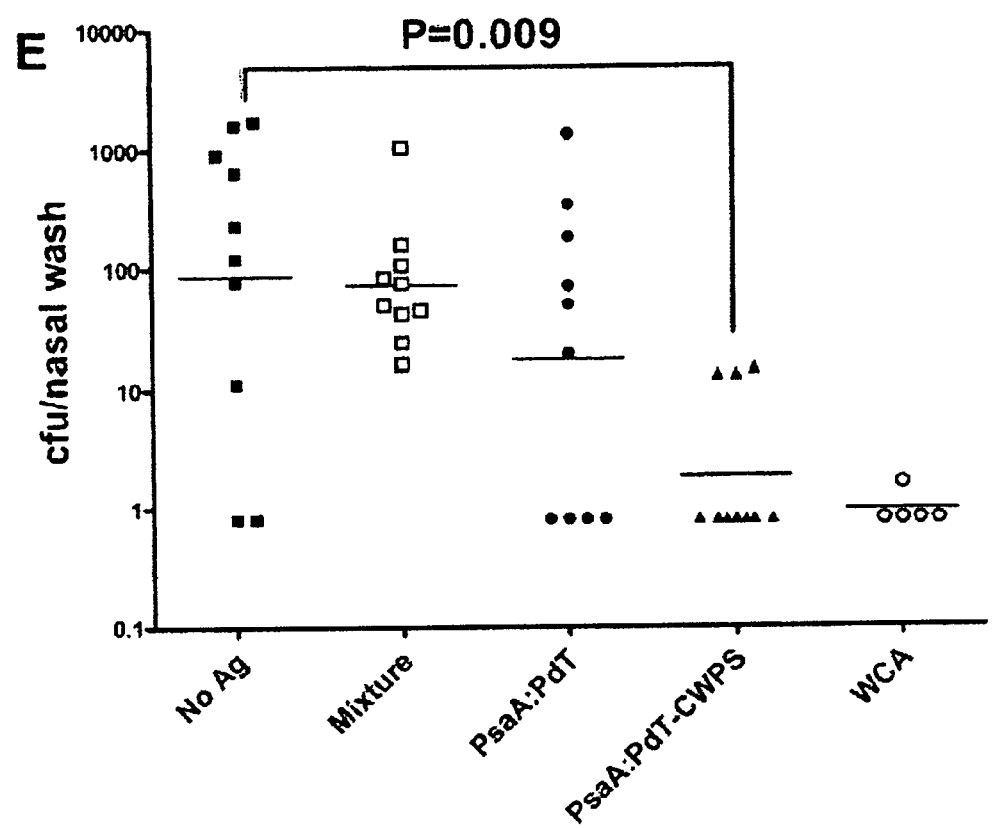

Priming for expression of IL-17A in vitro is shown in FIG. 4D. Priming for IL-17A production was assayed in vitro in cells from the three-week blood samples, incubated six days with pneumococcal whole cell antigen (WCA). No IL-17A was detected in cells incubated with DMEM culture medium only. The cells of conjugate-immunized mice produced IL-17A levels substantially higher than those immunized with the antigen mixture or the PsaA:PdT fusion protein and similar to cells from the mice immunized with the WCA. The results of challenge with serotype 6B pneumococci are shown in FIG. 4E. There was no significant protection by the mixture or the fusion protein (albeit a suggestion of activity by the latter) as compared to the CT adjuvant alone. In contrast, there was about 40-fold reduction in the geometric mean colonization of the conjugate-immunized mice (P=0.009). This protection was comparable to that produced by the pneumococcal WCA, known to be highly protective in this model (Malley et al., 2003).

Figure 5A:
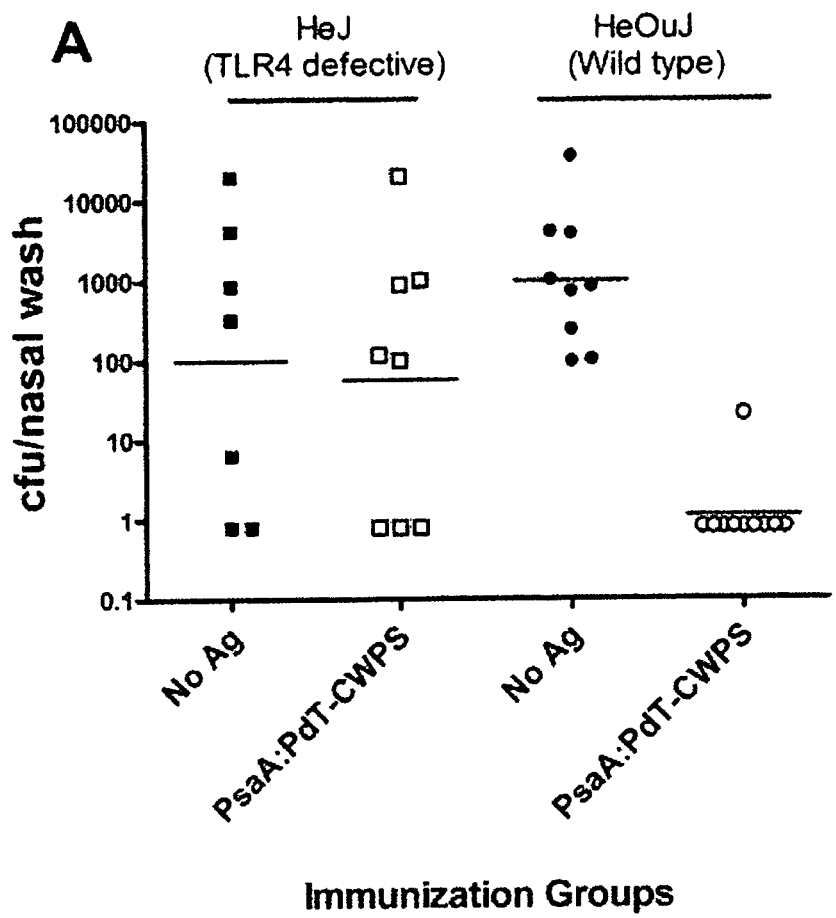
FIGS. 5A and 5B show protection conferred by fusion conjugate is dependent on TLR4.
Figure 5B:
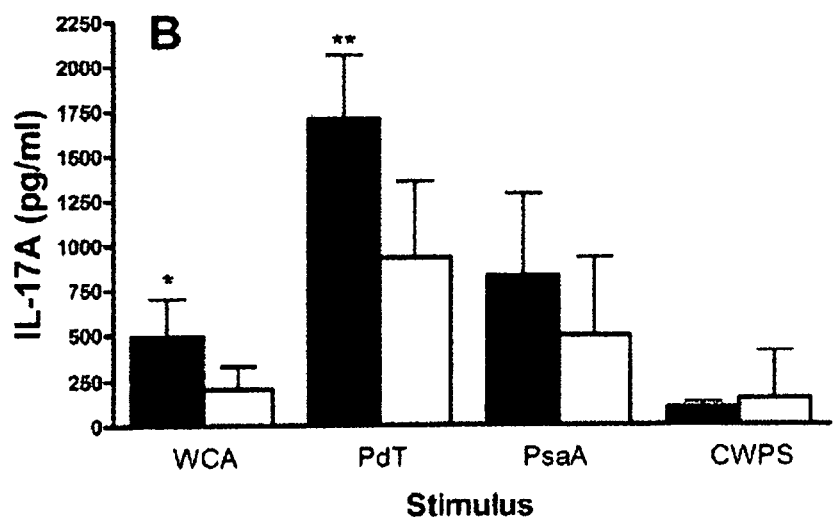

Protection by the fusion conjugate PsaA:PdT-CPS was found herein to be TLR4 dependent. To test whether protection by the fusion conjugate is TLR4 dependent, C3H/HeJ (TLR defective) and C3H/HeOuJ (wild type) mice were intranasally immunized then challenged as previously described with strain 0603. The fusion conjugate protected HeOuJ mice from colonization to the same extent as observed in C57/BL6 mice, but there was no protection observed in HeJ mice suggesting that protection by the fusion conjugate is TLR4-dependent (FIG. 5A). To investigate the mechanism behind this TLR4-dependent protection, antibodies to the whole cell antigen and IL-17A responses from splenocytes stimulated with WCA or the individual components of the fusion conjugate (PdT, CWPS, and PsaA) were measured in immunized HeJ and HeOuJ mice. No differences in antibody against WCA were noted between immunized HeOuJ and HeJ mice. In contrast, splenocytes from HeJ mice made significantly less IL-17A when stimulated with WCA or PdT (FIG. 5B). It was demonstrated previously that protection against NP colonization is mediated by, and correlates with, IL-17A production (Lu et al., 2008). Thus the lack of protection in HeJ mice may be explained by a requirement for TLR4 for priming for IL-17A responses, as has been shown by others (Kolls & Linden, 21 Immunity 467-76 (2004)).

Figures 6A, 6B:
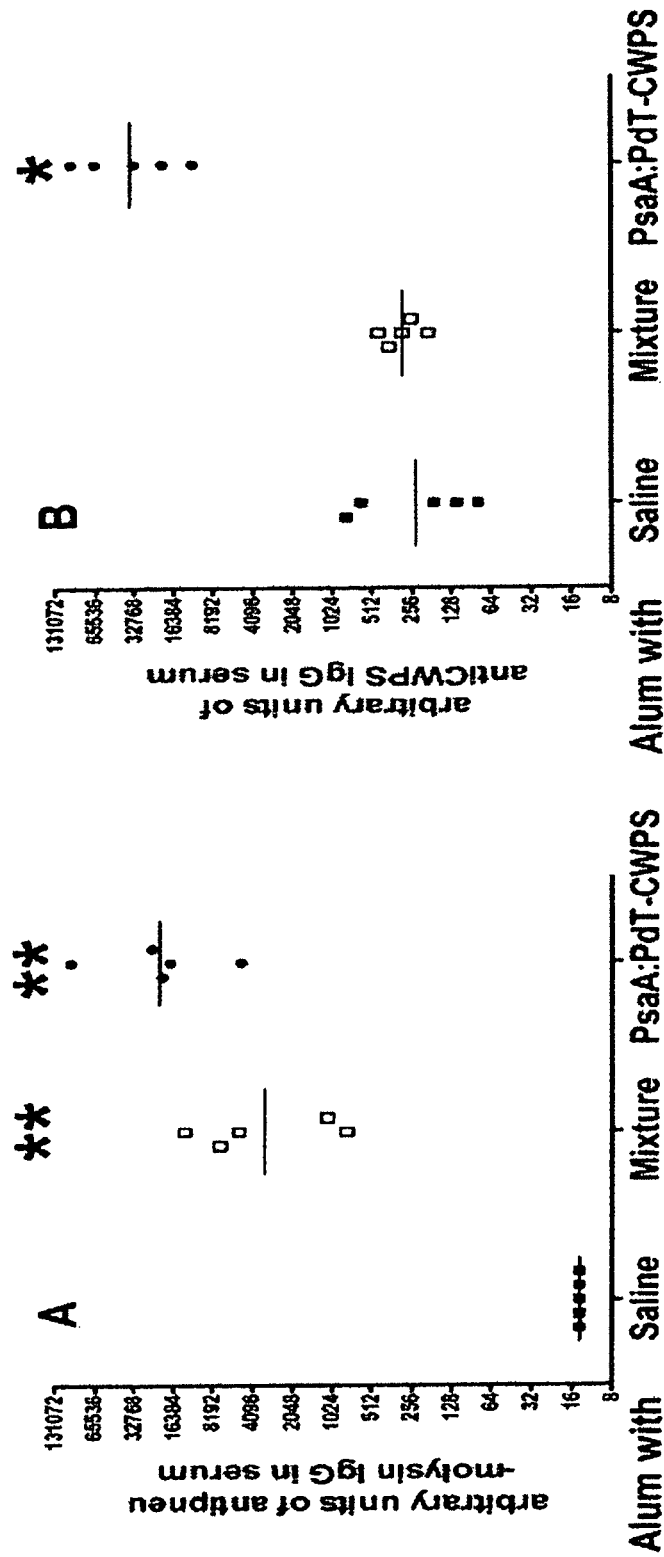
FIGS. 6A to 6D demonstrate the effect of subcutaneous vaccination on antibody production. Injections were given biweekly twice with 200 μg of alum as adjuvant. The antigen contained 7.7 μg of PdT, 14 μg of CWPS, and 5 μg of PsaA, given either as a mixture or as the fusion conjugate. The animals were bled two weeks after the last immunization, and serum IgG antibodies were measured against PdT (FIG. 6A), CWPS (FIG. 6B), PsaA (FIG. 6C), or the pneumococcal whole cell antigen, WCA (FIG. 6D). For all panels, horizontal lines represent geometric means and statistical analysis was performed using Mann-Whitney U test for comparison of titers in mice immunized with the fusion conjugate vs. the mixture. *$P<0.05$, **$P<0.01$ by Kruskal-Wallis test with Dunn's correction.
Figures 6C, 6D:
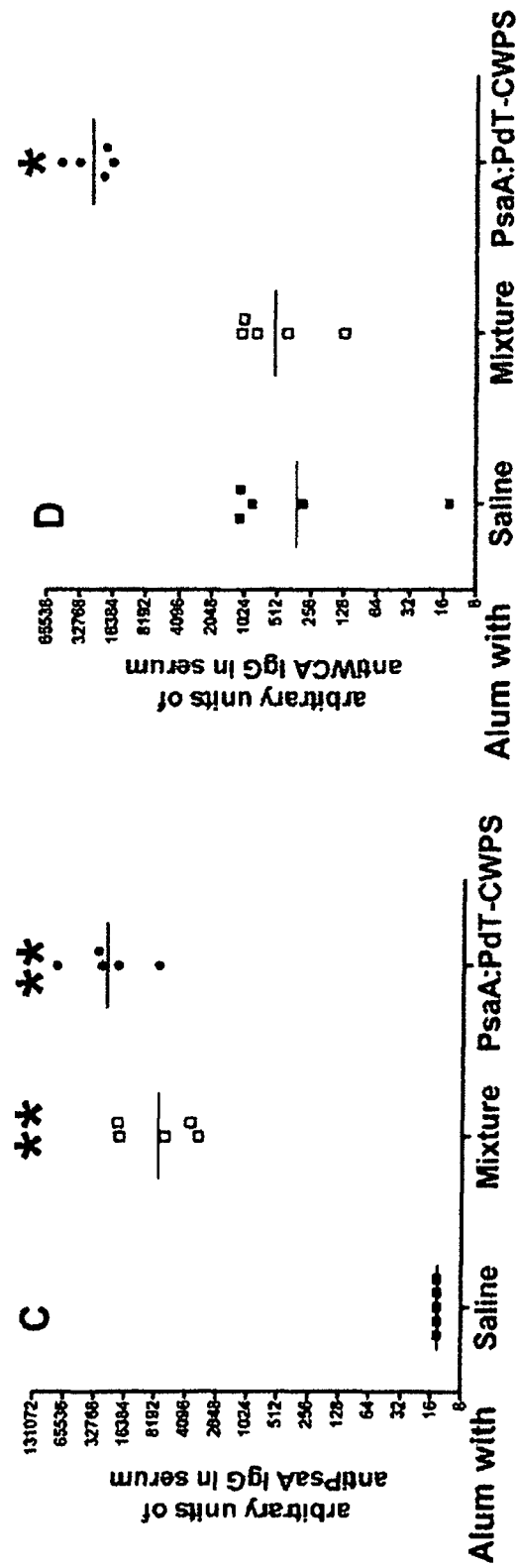
Figures 7A, 7B:
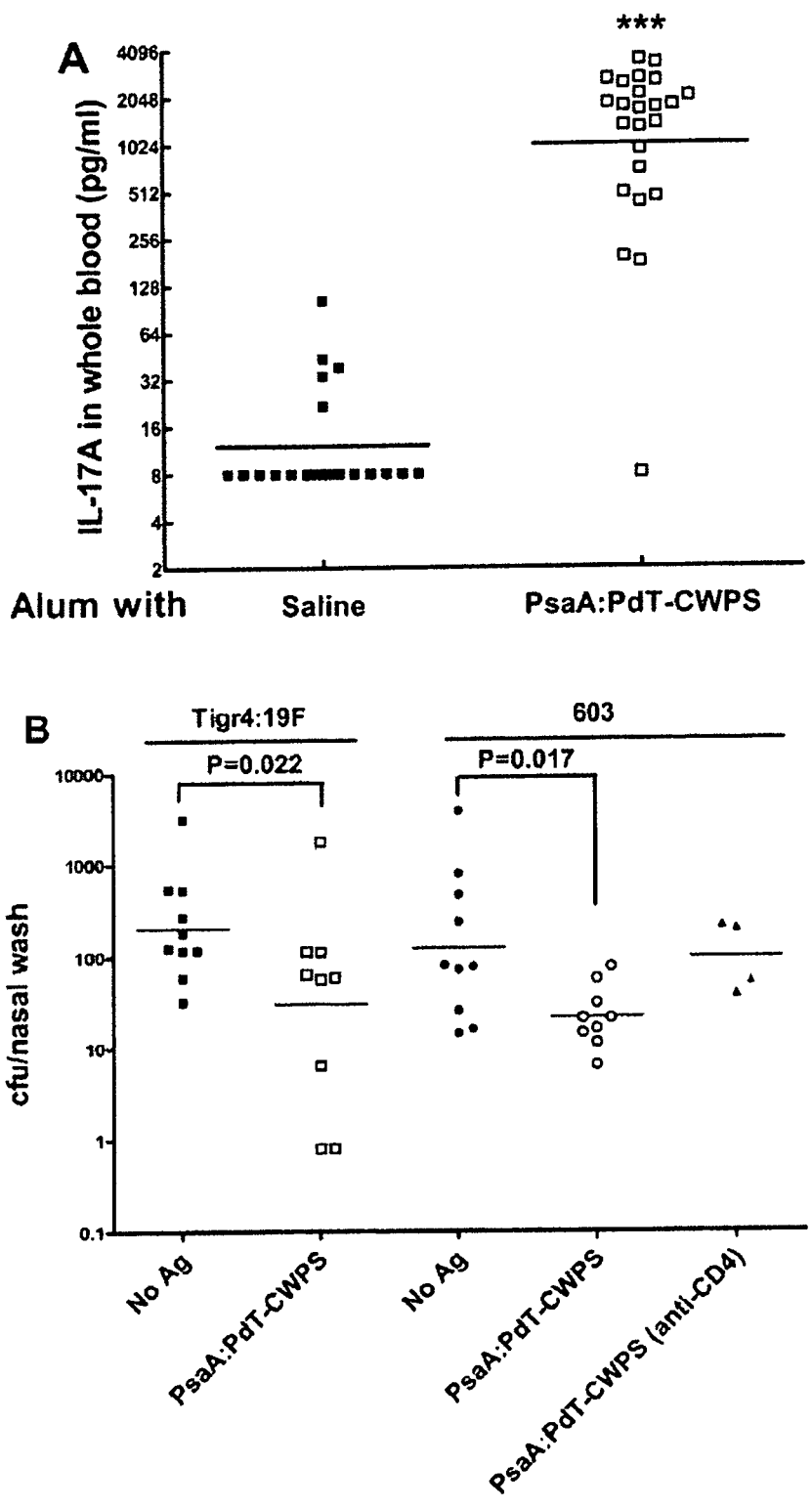
FIGS. 7A and 7B show the effect of subcutaneous vaccination on priming for IL-17A production and on colonization by serotypes 19F and 6B. Mice were immunized as in FIG. 6 except that one additional injection was given.

To examine the fusion conjugate as a systemic immunogen, mice were injected s.c. (two-week intervals, alum adjuvant) with the conjugate or the control mixture of PdT, CWPS, and PsaA. Antibodies were measured two weeks after the secondary immunization. The conjugate generated higher antibody titers than the mixture for all three antigens (6-fold higher for PdT, 140-fold higher for CWPS, and 3-fold higher for PsaA; FIGS. 6A to 6C). Antibody responses against WCA also were measured and were likewise greater (40-fold) after the conjugate (FIG. 6D). Thus the fusion conjugate strongly elicited antibodies to its component antigens in configurations expressed in the pneumococcal cell. Priming for IL-17A responses and protection against colonization were determined after three s.c. injections. Cells from the s.c.-vaccinated mice produced on average about 100-fold higher IL-17A than the CT control (FIG. 7A). The mice were nasally challenged (separately) with serotype 19F or serotype 6B. There was protection against both serotypes by about one log-fold compared to the alum controls (P<0.05, FIG. 7B). At the time of challenge with the serotype 6B strain, antibodies to murine CD4+ was administered to four mice previously immunized with the fusion conjugate; as a result, protection was abrogated in this group, suggesting that CD4+ T cells (and likely IL-17A) are responsible for this protection.

Figure 8:
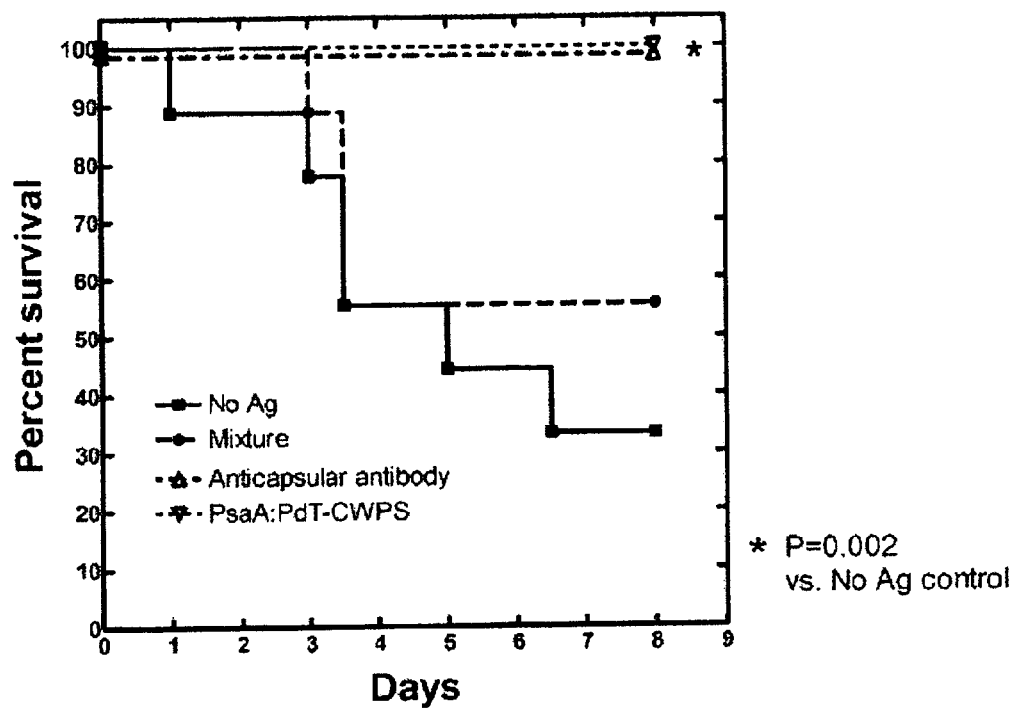
FIG. 8 is a graph showing protection by the fusion conjugate administered subcutaneously in a model of fatal aspiration pneumonia. The conjugate or antigen mixture was injected with alum as in FIG. 6. Three weeks post-immunization, a positive control group was given capsular antibody passively, then all animals were colonized by nontraumatic intranasal inoculation with $10^6$ c.f.u. serotype 3 strain WU2. Three days later, mice were made to inhale WU2 into the lung and monitored twice daily. Deaths were noted, and sick animals were euthanized and their blood cultured. All the sick mice had pneumococci in the blood, and thus were counted as non-survivors. Differences in survival were compared using the Kaplan Meier test.

Possible protection against invasive disease was tested using a fatal aspiration pneumonia model with serotype 3 strain WU2 (Malley et al., 74 Infect. Immun. 2187-95 (2006)). FIG. 8 shows that only 35% of the alum control mice survived. Survival of mice immunized with the antigen mixture 55%) was not significantly different. In contrast, 100% of mice vaccinated with the conjugate survived (P<0.002 vs. alum controls by Kaplan-Meier).

Protection by the extant 23-valent capsular polysaccharide vaccine depends upon immunological maturity. In general, the vaccine is not effective for subjects under two years old. Broad use of the 7-valent capsular conjugate vaccine (PCV7) has greatly reduced pneumococcal disease, but the limited serotypes in PCV7 limit the vaccine's efficacy for most developing countries, and non-vaccine type serotype replacement has been reported in the U.S.

One embodiment of the present invention provides for a new conjugate vaccine candidate that contains CWPS and a fusion protein of PsaA and PdT, and protects against pneumococcal colonization and diseases in both in vitro and in vivo models. Additionally, this vaccine should confer protection against all serotypes because all the three components are conserved in pneumococcus.

Moreover, conjugation of CWPS to the fusion protein enhanced antibody responses to PsaA, both from intranasal immunization and subcutaneous immunization. The immunization with conjugate also enhanced T-cell responses. Further, the conjugate vaccine resulted in TLR4 dependent protection against colonization: following subcutaneous immunization, the fusion protein conjugate is more immunogenic and resulted in a 90% reduction in pneumococcal colonization density, and also protected mice from lethal lung inhalation challenge with serotype 3 strain pneumococcus.

Other implications of the present invention include: the fusion of a target protein (PsaA) to the TLR4 agonist PdT and subsequent conjugation of the fusion protein to the conserved zwitterionic polysaccharide CWPS resulted in significantly higher immune responses to the target protein. These results suggest strongly that the construction of a conjugate consisting of CWPS conjugated to pneumolysoid fused with a target protein (i.e., an antigen) should result in greatly enhanced immunity to the target protein. These results are generalizable to other proteins (beyond PsaA, involving pathogens other than pneumococcus). For example, the target proteins StkPR, PcsB, and StkP where found to have enhanced immunogenicity when presented as a PdT fusion conjugated to CWPS. In this sense, the construct/conjugate serves to augment the immune response to the protein, and may act as an effective adjuvant for vaccine development.

The CWPS of the present invention may be generated by any method known in the art (see, e.g., Slade, 90(3) J. Bacterial. 667-72 (1965)), and the polysaccharide (PS) of non-pneumococcal bacteria may be used as well. For example, the PS of *Bacillus anthracis* is species specific (Choudhury et al., 281(38) J. Biol. Chem. 27932-41 (2006)), and may serve as an antigenic component. Similarly, the PS of the gram-negative bacteria *Brucella abortus* and *B. melitensis* are highly antigenic and well characterized (see, e.g., Rose et al., 2 Protein Sci. 1106-13 (1993). Additionally, a portion of the CWPS, or a mimetic of the CWPS may be incorporated into a pneumococcal vaccine. Conjugate protein-PS vaccines, including those comprising streptococcal and pneumococcal PS are well-known in the art and provide for methods of conjugation. See e.g., U.S. Pat. No. 6,248,570; No. 5,866,135; No. 5,773,007. CWPS mimotopes, such as protein or peptide mimetics of polysaccharide molecules, are also possible alternative antigens or immunogens (see, e.g., Pincus et al., 160. J. Immunol. 293-98 (1998); Shin et al., 168 J. Immunol. 6273-78 (2002)). Additionally, other proteins or nucleic acids of may serve as antigens or immunogens in vaccine or vaccine development using any number of techniques known in the art. See, e.g., U.S. Pat. No. 6,936,252.

Various pneumolysin mutants are also known in the art and within the scope of the present invention, including combinations of one or more His367Arg, Cys428Gly, Cys428Ser, Trp433Phe (Pdb toxoid), Glu434Gln, Trp435Phe, Asp385Asn, His156Tyr, His367Arg, and Cys428Gly. See, e.g., U.S. Pat. No. 6,716,432. Any appropriate pneumolysin mutant may be suitable for the present fusion-conjugate, as long as they retain the immunogenic nature of pneumolysin but have reduced or undetectable hemolytic activity compared to native pneumolysin (Kirkham et al., 74(1) Infect. Immun. 586-93 (2006); U.S. Pat. No. 6,764,686). Additionally, a fragment or portion of such a pneumolysin is also suitable for the present invention.

PspA is also well known in the art, as is PspC. An immunogenic region of these proteins has recently been identified, lacking alpha helical structure (WO/2007/089866). As noted above, the fusion-conjugate composition of the present invention may include any protein of interest, from cultured or recombinant sources, or a fragment of such proteins.

One or more adjuvant agents may be included in such vaccines, as are accepted in the art, such as those described herein and, for example, *E. coli* mutant enterotoxin (U.S. Pat. No. 6,019,982), cytokines and complement (Gor et al., 70(10) Infect. Immun. 5589-95 (2002)), or neisserial porins (U.S. Pat. No. 6,613,336).

The delivery of pneumococcal vaccines and other vaccines, either by parenteral, mucosal, or other administration, as well as the design, monitoring, and dosing regimens of such vaccines are also well-known in the art.

Additionally, the conjugate of the present invention may be useful in vaccine development because it may be used to characterize the response at the cellular or molecular level. Sera or antibodies raised to the conjugate may also be used for passive protection. The antibodies useful for passive immunization may be raised initially against the present fusion-conjugate, but also includes both intact immunoglobulin molecules as well as portions, fragments, peptides and derivatives thereof, such as, for example, Fab, Fab', F(ab')$_2$, Fv, CDR regions, or any portion or peptide sequence of the antibody that is capable of binding antigen or epitope. An antibody is said to be "capable of binding" a molecule if it is capable of specifically reacting with the molecule to thereby bind the molecule to the antibody. The methods of generating such molecules are also well-known in the art.

Embodiments of the present invention are described further by these non-limiting examples.

EXAMPLES

Example 1

Construction of an Immunogenic Conjugate

Materials.

"Pneumococcal cell-wall polysaccharide, purified" (CWPS) was from Statens Seruminstitut, Copenhagen, Denmark. It was prepared from strain CSR SCS2 as described previously (Karlsson et al., 265(3) Eur. J. Biochem. 1091-97 (1999)). Pneumococcal whole-cell antigen (WCA) consists of ethanol-killed cells of a capsule-deficient pneumococcus strain RxIAL—as previously reported (Malley, et al., 69 Infect. Immun. 4870-73 (2001)). Cholera toxin (CT) was from List Biological Laboratories (Campbell, Calif.). The monoclonal antibody to the PCho determinant of CWPS (TEPC-15), 1-Cyano-4-dimethylaminopyridinium tetrafluoroborate (CDAP), triethylamine (TEA), and ethanolamine (EA) were from Sigma (St. Louis, Mo.). Other chemicals used are of analytical grade.

Protein Purification.

*S. pneumoniae* nonhemolytic variant of pneumolysin (PdT) with mutations W433F, D385N and C428G, which render the molecule nontoxic but do not interfere with TLR4-mediated inflammatory properties (Berry et al., 63(5) infect. Immun. 1969-74 (1995)), was purified from *E. coli* msbB mutant stain carrying a pQE30 vector that expresses Pdt (Srivastava et al., 2005). PsaA was a gift from Dr. Edwin Ades, CDC, (Atlanta, Ga.) (Srivastava et al., 19(1) Hybridoma, 23-31 (2000); De et al., 419(2) Arch. Biochem. Biophys. 147-57 (2003)). PsaA and PdT fusion protein PsaA:PdT was generated by linking *S. pneumoniae* truncated PsaA with PdT with a GSGGGGS linker.

Briefly, PsaA was amplified from *S. pneumoniae* genomic DNA by primers 5'-GGGGATCCAGCGGAAAAAAA-GATACAACTTCTGGTC-3' (SEQ ID NO:2) and 5'-GCG-GATCCACCTCCACCACTACCITTTGC-CAATCCTTCAGCAATC-3' (SEQ ID NO:3). The resulting truncated PsaA lacks N-terminus signal peptide and transmembrane domain and has a GSGGGGS (SEQ ID NO:1) in the C-terminus. This DNA piece was inserted between the 6His-tag and the starting codon of PdT and sequence of the final product was verified in Children's Hospital (Boston, Mass.) molecular genetics core facility.

*E. coli* cells were cultured in LB medium with antibiotic at 37° C. until the $OD_{600}$ reached 0.6. Cultures were cooled to room temperature and induced with isopropyl-1-thio-β-d-galactopyranoside, added to a final concentration of 1 mM, and incubation continued at room temperature for overnight. Then, cells were collected by centrifugation (6,000 rpm, 4° C., 15 min) and cell pellets were lysed with sonication. Soluble proteins were applied to a Ni2+-agarose column and washed with 40 mM imidazole, 20 mM Tris-HCl, pH 7.4, 0.5 M NaCl. His-tagged proteins were eluted with 10 mM EDTA. Purified proteins were dialyzed against PBS extensively. Proteins were then treated with ETCLEAN™ beads (Cellufine, MA) to remove any residual LPS contamination.

Conjugation of CWPS to Proteins.

Proteins were conjugated to CWPS using 1-cyano-4-dimethylaminopyridinium tetrafluoroborate (CDAP), as described previously (Lees et al., 14(3) Vaccine, 190-98 (1996)). Briefly, 5 mg of CWPS was solubilized in saline at 10 mg/ml; 10 mg of CDAP (100 mg/ml in acetonitrile) was added while vortexting; 30 sec later, 100 μl 0.2 M TEA was added into mixture; 5 mg protein was added into mixture after 2 min. Reaction was carried out overnight at 4° C. and terminated with 100 μl 1M EA. The reaction mixture was applied to a Sepharose S300 column, eluted with PBS, and protein-conjugate was separated by collecting void volume fractions. Protein concentration was determined by BCA kit (Pierce) and CWPS content was determined by anthrone method (Roe, 212(1) J. Biol. Chem. 335-43 (1955)). The composition of the protein-polysaccharide conjugates in the constructs was as follows: PdT-CWPS conjugate protein:CWPS ratio 4:5; PsaA-CWPS conjugate protein:CWPS ratio 1:2; and PsaA:PdT-CWPS conjugate, ratio 1:1.1.

Example 2

In Vitro Analysis of Immunogenic Conjugate

Assay of IL-17A Production in Whole Blood Samples.

Fifty (50) μl of heparinized blood was added to 450 μl DMEM (BioWhittaker, Walkersville, Md.) containing 10% low-endotoxin defined FBS (Hyclone, Logan, Utah) and Ciprofloxacin (10 μg/ml, Cellgro, Manassas, Va.). Except for the unstimulated control, the cultures were incubated at 37° C. for six days with $10^7$ cells of pneumococcal WCA or with purified antigens as specified. Supernatants were collected following centrifugation and stored at −80° C. until analyzed by ELISA for IL-17A concentration (R&D Systems, Minneapolis, Minn.).

TNFα Production in Cultured Macrophage.

Wildtype and TLR4 knockout macrophage cell lines were gifts from University of Massachusetts. Cells were seeded at $1\times10^5$/ml in 96-well plates and incubated at 37° C. overnight. Medium was changed and 36 nM of each stimulus was added into each well and continued to incubate for 20 hr before supernatant was analyzed by ELISA for TNFα production.

Enzyme-Linked Immunosorbent Assay (ELISA).

Assays for murine antibodies to PdT and PsaA were done in Immulon 2 HB 96 microwell plates coated with either PdT or PsaA proteins (1 μg/ml). Assays for murine antibodies to CWPS was done in NUNC-immuno 96-microwell plates (Nalge Num Intl, Rochester, N.Y.) coated overnight with CWPS (5 μg/ml). Plates were blocked with 0.05% casin amino acid (PdT) or 5% fetal calf serum (PsaA and CWPS) in phosphate-buffered saline-0.05% Tween (PBS-T). Antibody diluted in PBS-T was added and incubated at room temperature for 2 hr. Plates were washed with PBS-T, and secondary antibody to mouse immunoglobulin G (Sigma) was added and incubated at room temperature for 1 hr. The plates were washed and developed with SureBlue TMB microwell peroxidase substrate (KPL, Gaithersburg, Md.). Antigenicity of CWPS derivatives was assayed by inhibition of the ELISA in which mouse monoclonal antibody to PCho (TEPC-15, Sigma) was premixed with serial dilutions of CWPS or the modified antigens before application to the CWPS coated plates as described previously (Malley et al., 2006).

Neutralization of Pneumolysin.

A neutralization assay was developed to evaluate whether antibodies against pneumolysin may have the capacity to neutralize the hemolytic activity of the molecule. Briefly, 100 μl of a solution containing pneumolysin at 100 ng/ml in PBS/0.1% BSA with 100 μM dithiothreitol (DTT, Sigma) was incubated for 30 min at 37° C. with serial dilutions of serum from mice immunized s.c. three times with the fusion conjugate or alum alone. Following this incubation, 50 μl of sheep red blood cells were added and incubated for another 30 min in the same conditions. After centrifugation at 2000 g for 5 min, supernatants were harvested and their OD420 measured to quantify hemolysis. These values were read against a standard consisting of 2-fold diluted samples of fully hemolyzed red blood cells; then compared with the dilution of serum at which 50% hemolysis was observed between groups.

Example 3

Immunization and Challenge of Mice

Mice were obtained from The Jackson Laboratories (Bar Harbor, Me.) unless otherwise noted. C57BL/6J (or HeOuJ) were used as wild-type animals and are referred to as "mice". The age at time of first immunization was between four to six weeks. Intranasal injection was done by instilling 10 μl of saline, adjuvant only, or adjuvant mixed with antigen as specified atraumatically into unanesthetized mice, a procedure that puts no immunogen into the lungs; secondary immunizations were given after one week. The amounts of all antigens applied to mice were all normalized to 5 μg PsaA per mouse. Subcutaneous immunization was done by mixing the antigen with 200 μg of alum (Alum Hydroxide, Accurate Chem. & Scientific Co, Westbury, N.Y.) on a volume of 200 μl and injection into the dorsal surface of the mouse. The amounts of all antigens were normalized to 5 μg PsaA per mouse.

To determine susceptibility to NP colonization, i.n. challenge with live encapsulated pneumococci was done as described (Malley et al., (2001). Four weeks after the second immunization, mice were i.n. challenged with $10^8$ colony-forming units (cfu)/ml serotype 6B strain 0603 containing predominantly transparent phenotype (Weiser et al., 62(6) Infect, Immun. 2582-89 (1994)), or of a strain of serotype 19F in the TIGR4 background (Trzcinski et al., 69 Appl. Environ. Microbiol. 7364-70 (2003)), in 10 μl PBS as described herein.

To examine whether protection against colonization was CD4+ T cell dependent, a small subset of mice received intraperitoneal injections of 0.35 mg of rat anti-mouse CD4 monoclonal IgG2b (purified from hybridoma GK1.5, American Type Culture Collection [ATCC], Manassas, Va.) one day prior to and on day three of challenge as described previously (Basset et al., 2007; Malley et al., 2005).

To determine NP colonization, an upper respiratory culture was done by instilling sterile saline retrograde through the transected trachea, collecting the first six drops (about 0.1 ml) from the nostrils, and plating neat or diluted samples on blood agar plates containing 2.5 μg gentamicin/ml; thus 1 cfu/100 μl of wash fluid or 10 cfu/ml was detectable. For calculations of geometric means, a sterile sample was assigned half the lower limit of detection, or 5 cfu/ml. As a model for pneumonia and sepsis, the heavily capsulated serotype 3 strain WU2 (Briles et al., 153(3) J. Exp. Med. 694-705 (1981)), was used. The mice were given $10^6$ cfu in 10 μl of phosphate-buffered saline i.n. to establish NP colonization; after two days, to mimic the aspiration of pneumococci, the mice were anesthetized with isoflurane and given an additional dose of $10^6$ cfu of WU2 in 100 μl by i.n. route. In control animals, this challenge produced death within four-to-five days in most mice, and bacteremia in all mice.

Statistical Analysis.

NP colonization density was compared by the Mann-Whitney U test or by the Kruskal-Wallis test with Dunn's correction for multiple comparisons using PRISM (version 4.0a, GraphPad Software, Inc). Survival analysis by Kaplan Meier was performed using PRISM as well.

Example 4

Fusion to PdT-CWPS Confers Immunogenic Synergy for X

Three conjugates of X:PdT-CWPS were prepared as discussed in the preceding examples. More specifically, in one immunogenic preparation, the PdT was fused to the C-terminal pneumococcal polypeptidepeptide StkP (Serine/Threonine Protein Kinase), which has the amino acid sequence:

```
                                          (SEQ ID NO: 4)
YLILLASLVLVAASLIWILSRTPATIAIPDVAGQTVAEAKATLKKANFE

IGEEKTEASEKVEEGRIIRTDPGAGTGRKEGTKININVSSGKQSFQISN

YVGRKSSDVIAELKEKKVPDNLIKIEEEESNESEAGTVLKQSLPEGTTY

DLSKATQIVLTVAKKATTIQLGNYIGRNSTEVISELKQKKVPENLIKIE

EEESSESEPGTIMKQSPGAGTTYDVSKPTQIVLTVAKKVTSVAMPSYIG

SSLEFTKNNLIQIVGIKEANIEVVEVTTAPAGSAEGMVVEQSPRAGEKV

DLNKTRVKISIYKPKTTSATP
```

In another immunogenic preparation, PdT was fused to the N-terminal pneumococcal PcsB protein (derived from pcsB, which encodes the protein required for cell separation in group B streptococci), which has the sequence:

```
                                          (SEQ ID NO: 5)
ETTDDKIAAQDNKISNLTAQQQEAQKQVDQIQEQVSAIQAEQSNLQAEN

DRLQAESKKLEGEITELSKNIVSRNQSLEKQARSAQTNGAVTSYINTIV

NSKSITEAISRVAAMSEIVSANNKMLEQQKADKKAISEKQVANNDAINT

VIANQQKLADDAQALTTKQAELKAAELSLAAEKATAEGEKASLLEQKAA

AEAEARAAAVAEAAYKEKRASQQQSVLASANTNLTAQVQAVSESAAAPV

RAKVRP
```

Another immunogenic construct fused PdT with a polypeptide StkPR (Serine/Threonine Protein Kinase repeat unit), which has the amino acid sequence:

```
                                          (SEQ ID NO: 6)
VTSVAMPSYIGSSLEFTKNNLIQIVGIKEANIEVVEVTTAPAGSAEGMV

VEQSPRAGEKVDLNKTRVKISIYKPKTTSATP
```

These recombinant constructs were conjugated to CWPS as described. Immunization groups were given subcutaneous injections of either the conjugate preparation, or equimolar mixtures of the same antigens. Subsequently, elicited IgG was compared for antigen "X." Each of the conjugates elicited more IgG than did the corresponding mixtures. FIG. 9.

Example 5

Immunogenic Constructs Including Dextran

Groups of ten C57BL/6 mice each were immunized subcutaneously with one of the following, three times, two weeks apart: (1) alum alone; (2) CWPS-PdT:PsaA (fusion protein of PdT:PsaA conjugated to CWPS); and (3) PsaA:PdT-Dextran (fusion protein of PdT:PsaA conjugated to dextran (35 kD)).

Antibody responses to the X protein (represented here by PsaA) and also T-cell responses (both IL-17A and IFNγ) were evaluated and compared with the response to whole pneumococci as well as purified proteins.

Figure 10A:
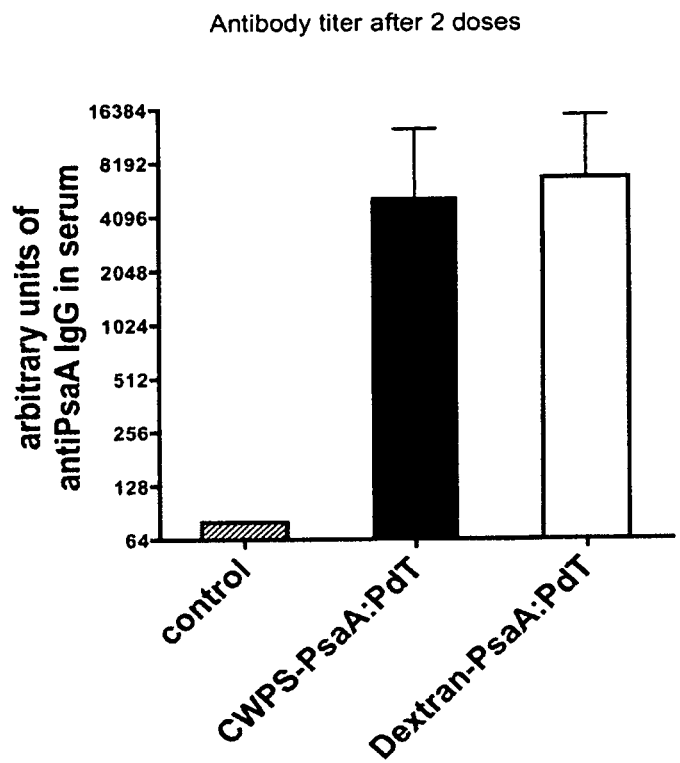
FIG. 10 shows antibody titers to PsaA in conjugates comparing CWPS with dextran. Mice were immunized three times, two weeks apart, with vaccine preparations as indicated (alum control, PsaA:PdT-CWPS or PsaA:PdT-Dextran). Blood samples were obtained two weeks after the second (FIG. 10A) and third immunizations (FIG. 10B), and serum analyzed by ELISA for the titer of IgG antibodies directed against PsaA. Mice immunized only with alum control had essentially undetectable antibodies. Mice immunized with the dextran-containing conjugate did not have lower antibody titers ($P>0.2$) than mice immunized with the CWPS-containing conjugate after either two or three doses. Median and interquartile range are shown. N=10 per group.
Figure 10B:
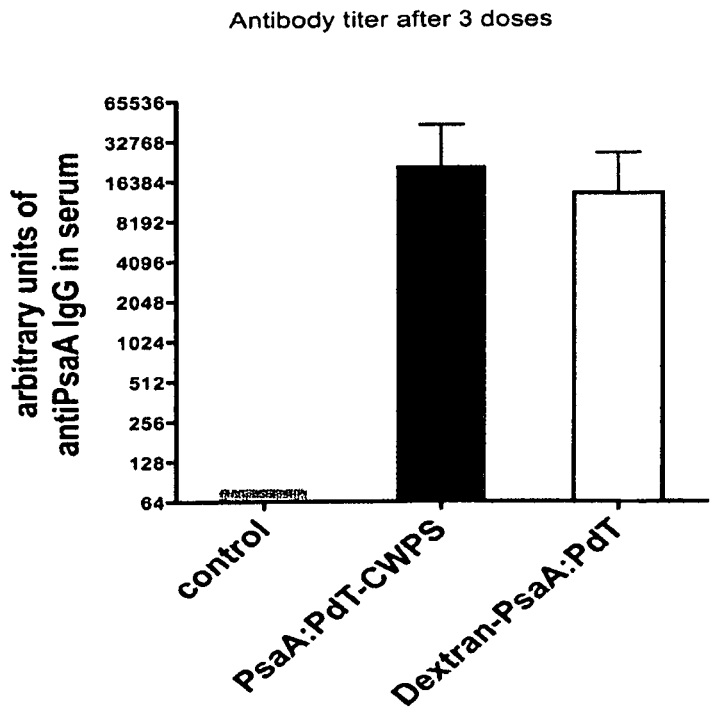

Antibody Titers to PsaA (the X in the Construct):

Mice were immunized three times, two weeks apart with vaccine preparations as indicated (alum control, CWPS-PsaA:PdT or Dextran-PsaA:PdT). Blood samples were obtained two weeks after the second and third immunization and serum analyzed for the titer of IgG antibodies directed against PsaA by ELISA. Mice immunized only with alum/control had essentially undetectable antibodies. Mice immunized with the dextran-containing conjugate did not have lower antibody titers (P>0.2) than mice immunized with the CWPS-containing conjugate after either two or three doses as shown in FIG. 10. Median and interquartile range are shown. N=10 per group.

Figure 11A:
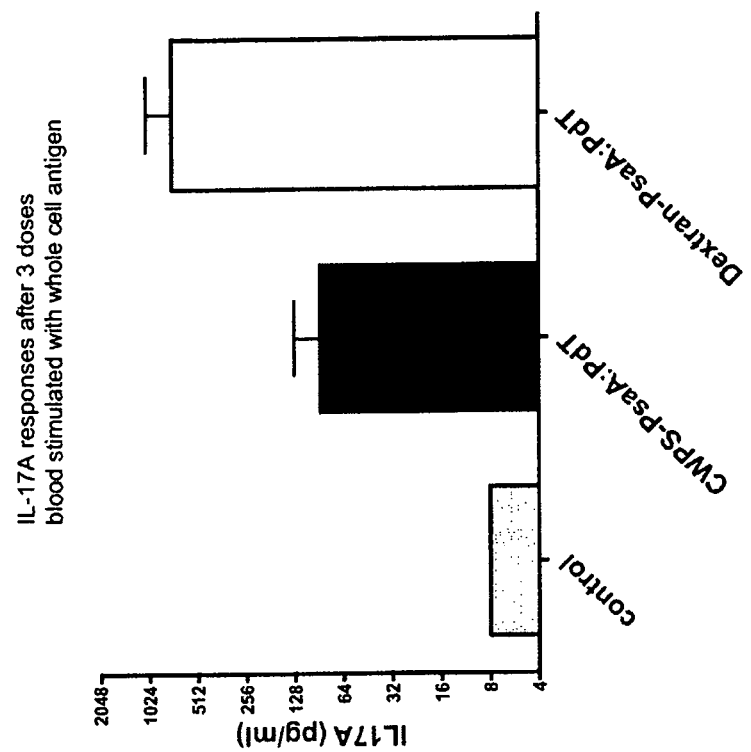
FIG. 11A shows IL-17A responses after two or three doses for blood stimulated with whole cell pneumococcal antigen.
Figure 11A:
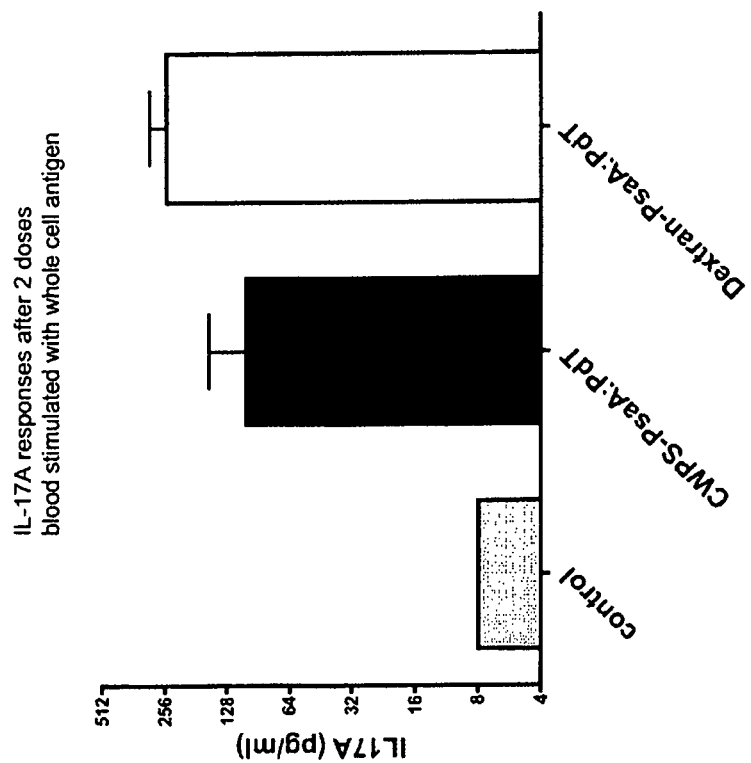
Figure 11B:
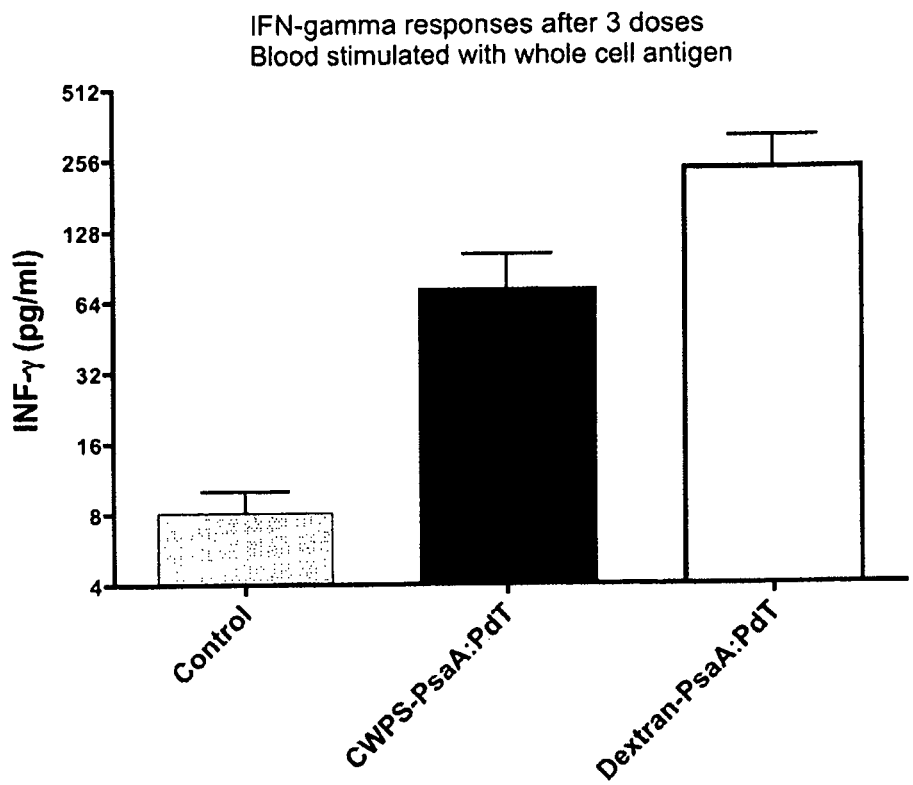
FIG. 11B shows IFNγ responses after three doses in blood stimulated with killed pneumococcus.
Figure 11C:
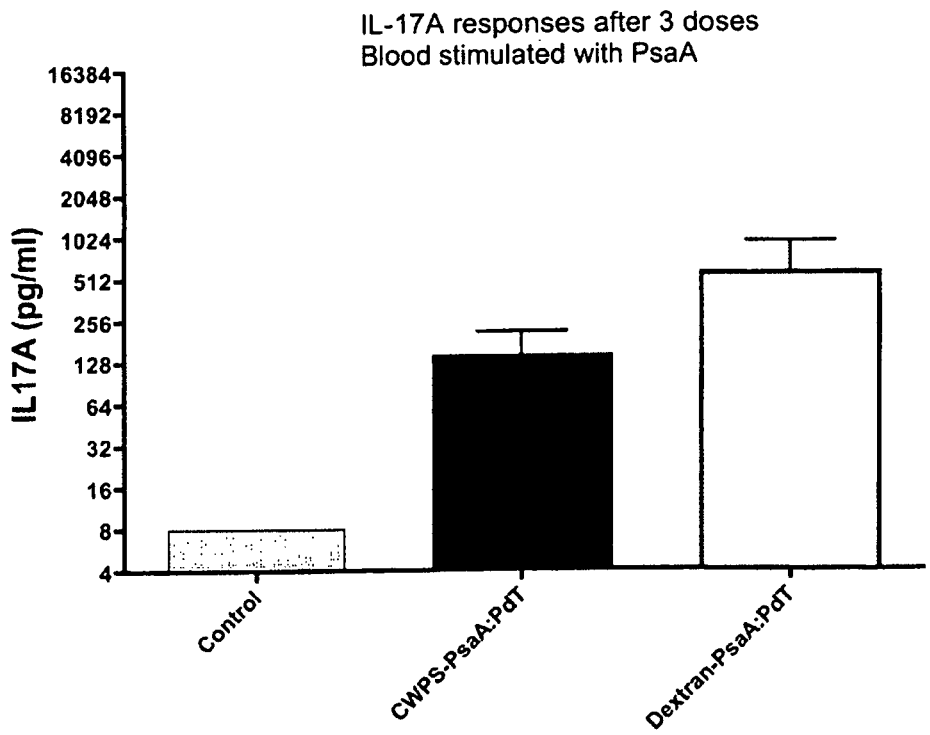
FIG. 11C shows IL-17A responses after three doses in blood stimulated with PsaA.
Figure 11D:
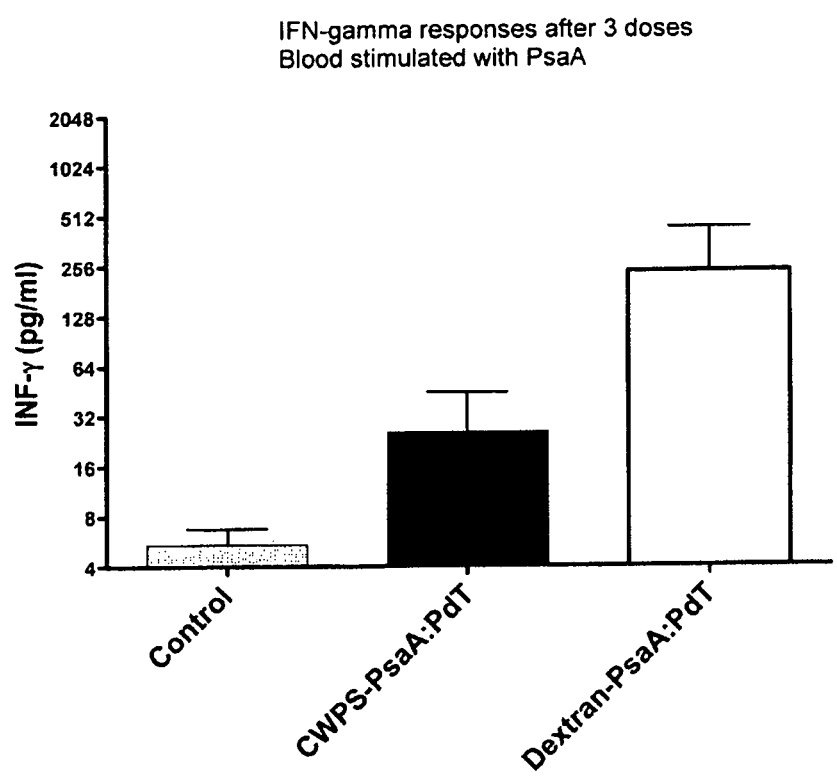
FIG. 11D shows IFNγ responses after three doses for blood stimulated with PsaA.

T Cell Responses:

Same immunization scheme and groups. Two weeks after second and third immunization, whole blood of mice was sampled and stimulated as indicated to measure T-cell cytokine (IL-17A and IFNγ) responses. Mean and SEM are shown, N=10 mice per group. FIG. 11A shows IL-17A responses after two or three doses for blood stimulated with whole cell pneumococcal antigen. FIG. 11B shows IFNγ responses after three doses in blood stimulated with killed pneumococcus. FIG. 11C shows IL-17A responses after three doses in blood stimulated with PsaA. FIG. 11D shows IFNγ responses after three doses for blood stimulated with PsaA.

Figure 12:
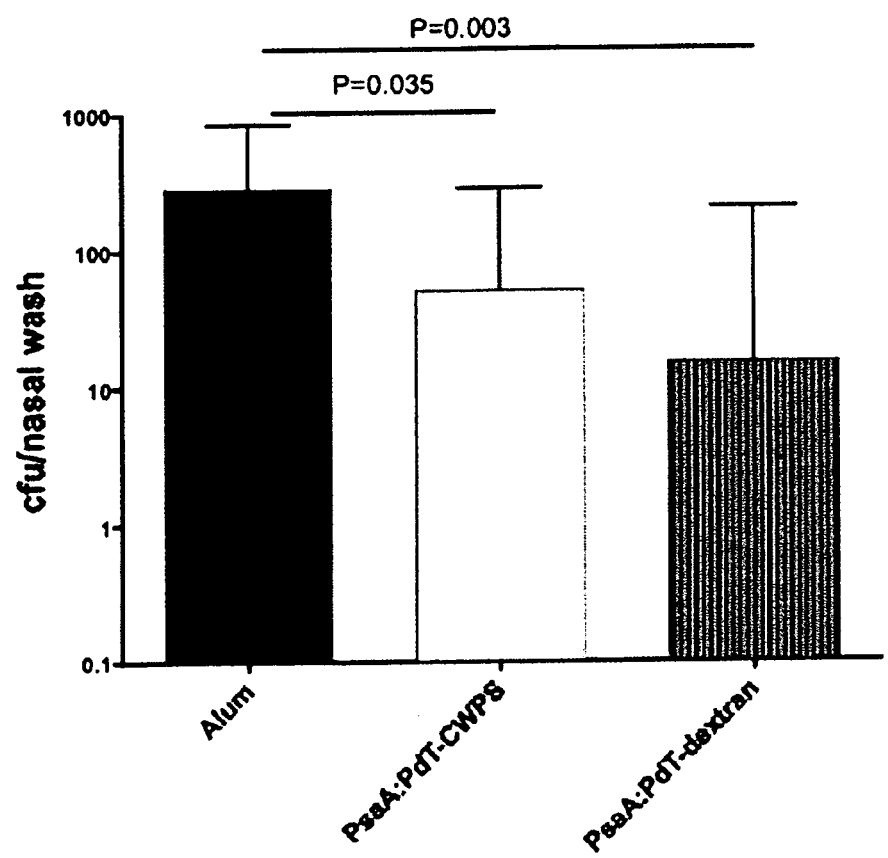
FIG. 12 shows colonization testing using the conjugates of FIG. 10. Two weeks after the last immunization, the mice were challenged intranasally with a clinical isolate of pneumococcus (strain 0603); colonization status was evaluated ten days later by determining density of bacteria in respiratory washes. Columns represent medians with interquartile range. P values by Mann Whitney test are shown.

Colonization Studies:

Two weeks after the last immunization, the mice were challenged intranasally with a clinical isolate of pneumococcus (strain 0603); colonization status was evaluated ten days later by determining density of bacteria in respiratory washes. Results are shown in FIG. 12. Both the CWPS- and Dextran-based conjugates were significantly protective against colonization, suggesting that either sugar may be used. There may be advantages (vs. other forms of pneumococcal infections, such as sepsis/meningitis) to have CWPS in the construct; conversely, making a conjugate with dextran may be easier (as the polysaccharide can be extremely pure).

The invention claimed is:

1. An immunogenic composition comprising a fusion protein-polysaccharide conjugate, wherein the conjugate consists of a bacterial cell wall polysaccharide conjugated to a cancer antigen:PdT fusion protein, where PdT is a non-hemolytic variant of pneumolysin and the cancer antigen is a target protein, wherein administration of the composition to a subject elicits humoral immunity and T-cell immunity or mucosal immunity to the cancer antigen.

2. An immunogenic composition comprising a fusion protein-polysaccharide conjugate consisting of a bacterial cell wall polysaccharide conjugated to a X:Pdt fusion protein where PdT is a nonhemolytic variant of pneumolysin and X is a target protein, such that immunity to X is enhanced, and wherein the polysaccharide is a cancer antigen.

3. An immunogenic composition comprising a fusion protein of a truncated pneumococcal PsaA protein and a non-hemolytic pneumolysin PdT protein, conjugated to a bacterial cell wall polysaccharide (CWPS).

4. The immunogenic composition of claim 1, wherein the nonhemolytic variant of pneumolysin is connected to the cancer antigen by a linker.

5. The immunogenic composition of claim 4, wherein the linker is a peptide linker or 1-cyano-4-dimethylaminopyridinium tetrafluoroborate (CDAP).

6. The immunogenic composition of claim 1, wherein the polysaccharide has a molecular mass of less than 500 kDa.

7. The immunogenic composition of claim 6, wherein the polysaccharide has a molecular mass of less than 70 kDa.

8. The immunogenic composition of claim 1, wherein the bacterial cell wall polysaccharide (CWPS) is a pneumococcal polysaccharide or a polysaccharide of prokaryotic or eukaryotic origin.

9. The immunogenic composition of claim 3, wherein the bacterial cell wall polysaccharide (CWPS) is a pneumococcal polysaccharide or a polysaccharide of prokaryotic or eukaryotic origin.

* * * * *

SEQUENCE LISTING

```
<160> NUMBER OF SEQ ID NOS: 24

<210> SEQ ID NO 1
<211> LENGTH: 7
<212> TYPE: PRT
<213> ORGANISM: Artificial
<220> FEATURE:
```

```
<223> OTHER INFORMATION: Linker

<400> SEQUENCE: 1

Gly Ser Gly Gly Gly Ser
1               5

<210> SEQ ID NO 2
<211> LENGTH: 36
<212> TYPE: DNA
<213> ORGANISM: Streptococcus pneumoniae

<400> SEQUENCE: 2
ggggatccag cggaaaaaaa gatacaactt ctggtc                              36

<210> SEQ ID NO 3
<211> LENGTH: 45
<212> TYPE: DNA
<213> ORGANISM: Streptococcus pneumoniae

<400> SEQUENCE: 3
gcggatccac ctccaccact acctttgcc aatccttcag caatc                     45

<210> SEQ ID NO 4
<211> LENGTH: 315
<212> TYPE: PRT
<213> ORGANISM: S. pneumoniae

<400> SEQUENCE: 4
```

Tyr Leu Ile Leu Leu Ala Ser Leu Val Leu Ala Ala Ser Leu Ile
1               5                   10                  15

Trp Ile Leu Ser Arg Thr Pro Ala Thr Ile Ala Ile Pro Asp Val Ala
            20                  25                  30

Gly Gln Thr Val Ala Glu Ala Lys Ala Thr Leu Lys Lys Ala Asn Phe
        35                  40                  45

Glu Ile Gly Glu Glu Lys Thr Glu Ala Ser Gly Lys Val Glu Glu Gly
    50                  55                  60

Arg Ile Ile Arg Thr Asp Pro Gly Ala Gly Thr Gly Arg Lys Glu Gly
65                  70                  75                  80

Thr Lys Ile Asn Leu Val Val Ser Ser Gly Lys Gln Ser Phe Gln Ile
                85                  90                  95

Ser Asn Tyr Val Gly Arg Lys Ser Asp Val Ile Ala Glu Leu Lys
            100                 105                 110

Glu Lys Lys Val Pro Asp Asn Leu Ile Lys Ile Glu Glu Glu Ser
        115                 120                 125

Asn Glu Ser Glu Ala Gly Thr Val Leu Lys Gln Ser Leu Pro Glu Gly
    130                 135                 140

Thr Thr Tyr Asp Leu Ser Lys Ala Thr Gln Ile Val Leu Thr Val Ala
145                 150                 155                 160

Lys Lys Ala Thr Thr Ile Gln Leu Gly Asn Tyr Ile Gly Arg Asn Ser
                165                 170                 175

Thr Glu Val Ile Ser Glu Leu Lys Gln Lys Val Pro Glu Asn Leu
            180                 185                 190

Ile Lys Ile Glu Glu Glu Glu Ser Ser Glu Ser Glu Pro Gly Thr Ile
        195                 200                 205

Met Lys Gln Ser Pro Gly Ala Gly Thr Thr Tyr Asp Val Ser Lys Pro
    210                 215                 220

Thr Gln Ile Val Leu Thr Val Ala Lys Lys Val Thr Ser Val Ala Met
225                 230                 235                 240

```
Pro Ser Tyr Ile Gly Ser Ser Leu Glu Phe Thr Lys Asn Asn Leu Ile
            245                 250                 255

Gln Ile Val Gly Ile Lys Glu Ala Asn Ile Glu Val Val Glu Val Thr
            260                 265                 270

Thr Ala Pro Ala Gly Ser Ala Glu Gly Met Val Val Glu Gln Ser Pro
            275                 280                 285

Arg Ala Gly Glu Lys Val Asp Leu Asn Lys Thr Arg Val Lys Ile Ser
290                 295                 300

Ile Tyr Lys Pro Lys Thr Thr Ser Ala Thr Pro
305                 310                 315

<210> SEQ ID NO 5
<211> LENGTH: 251
<212> TYPE: PRT
<213> ORGANISM: S. pneumoniae

<400> SEQUENCE: 5

Glu Thr Thr Asp Asp Lys Ile Ala Ala Gln Asp Asn Lys Ile Ser Asn
1               5                   10                  15

Leu Thr Ala Gln Gln Gln Glu Ala Gln Lys Gln Val Asp Gln Ile Gln
            20                  25                  30

Glu Gln Val Ser Ala Ile Gln Ala Glu Gln Ser Asn Leu Gln Ala Glu
            35                  40                  45

Asn Asp Arg Leu Gln Ala Glu Ser Lys Lys Leu Glu Gly Glu Ile Thr
50                  55                  60

Glu Leu Ser Lys Asn Ile Val Ser Arg Asn Gln Ser Leu Glu Lys Gln
65                  70                  75                  80

Ala Arg Ser Ala Gln Thr Asn Gly Ala Val Thr Ser Tyr Ile Asn Thr
            85                  90                  95

Ile Val Asn Ser Lys Ser Ile Thr Glu Ala Ile Ser Arg Val Ala Ala
            100                 105                 110

Met Ser Glu Ile Val Ser Ala Asn Asn Lys Met Leu Glu Gln Gln Lys
            115                 120                 125

Ala Asp Lys Lys Ala Ile Ser Glu Lys Gln Val Ala Asn Asn Asp Ala
130                 135                 140

Ile Asn Thr Val Ile Ala Asn Gln Gln Lys Leu Ala Asp Asp Ala Gln
145                 150                 155                 160

Ala Leu Thr Thr Lys Gln Ala Glu Leu Lys Ala Ala Glu Leu Ser Leu
            165                 170                 175

Ala Ala Glu Lys Ala Thr Ala Gly Glu Lys Ala Ser Leu Leu Glu
            180                 185                 190

Gln Lys Ala Ala Ala Glu Ala Glu Ala Arg Ala Ala Val Ala Glu
            195                 200                 205

Ala Ala Tyr Lys Glu Lys Arg Ala Ser Gln Gln Ser Val Leu Ala
            210                 215                 220

Ser Ala Asn Thr Asn Leu Thr Ala Gln Val Gln Ala Val Ser Glu Ser
225                 230                 235                 240

Ala Ala Ala Pro Val Arg Ala Lys Val Arg Pro
            245                 250

<210> SEQ ID NO 6
<211> LENGTH: 81
<212> TYPE: PRT
<213> ORGANISM: S. pneumoniae

<400> SEQUENCE: 6
```

```
Val Thr Ser Val Ala Met Pro Ser Tyr Ile Gly Ser Ser Leu Glu Phe
1               5                   10                  15

Thr Lys Asn Asn Leu Ile Gln Ile Val Gly Ile Lys Glu Ala Asn Ile
            20                  25                  30

Glu Val Val Glu Val Thr Thr Ala Pro Ala Gly Ser Ala Glu Gly Met
        35                  40                  45

Val Val Glu Gln Ser Pro Arg Ala Gly Glu Lys Val Asp Leu Asn Lys
    50                  55                  60

Thr Arg Val Lys Ile Ser Ile Tyr Lys Pro Lys Thr Thr Ser Ala Thr
65                  70                  75                  80

Pro
```

<210> SEQ ID NO 7
<211> LENGTH: 285
<212> TYPE: PRT
<213> ORGANISM: Chlamydia trachomatis

<400> SEQUENCE: 7

```
Met Thr Thr Pro Asp Asn Asn Thr Ile Asp Val Ser Phe Pro Thr Phe
1               5                   10                  15

Val Arg Leu Asn Val Ala Thr Thr Asp Leu Ala Asp Gly Asn Lys Ser
            20                  25                  30

Asn Ala Val Thr Ile Thr Glu Thr Ala Thr Ala Asn Tyr Val Asn Val
        35                  40                  45

Thr Gln Asp Leu Thr Ser Ser Thr Ala Lys Leu Glu Cys Thr Gln Asp
    50                  55                  60

Leu Ile Ala Gln Gly Lys Leu Ile Val Thr Asn Pro Lys Ser Asp Ile
65                  70                  75                  80

Ser Phe Gly Gly Arg Val Asn Leu Ala Asp Asn Thr Val Asn Tyr Ser
                85                  90                  95

Asn Gly Gly Ala Glu Val Ser Phe Thr Asn Ile Asn Ser Arg Gln Gly
            100                 105                 110

Lys Gln Tyr Val Pro Tyr Gly Leu Tyr Lys Asn Gly Glu Pro Lys Ile
        115                 120                 125

Ser Met Arg Ser Ala Leu Ser Gly Gly His Val Gly Ser Gly Asp Thr
    130                 135                 140

Gly Gly Trp Gly Ala Glu Val Leu Trp Asp Ala Tyr Thr Glu Gln Leu
145                 150                 155                 160

Lys Asp Met Thr Asp Gly Ala Val Thr Leu Asn Ser Ser Asn Arg Gly
                165                 170                 175

Lys Leu Ser Phe Thr Ala Ser Pro Glu Ala Pro Val Leu Phe Arg Leu
            180                 185                 190

Ser Val Phe Met Arg Lys Asn Gly Asp Trp Leu Asp Asn Gly Val Gly
        195                 200                 205

Gly Arg Val Met Leu Tyr Val Asn Thr Asp Ser Ala Gly Lys Thr
    210                 215                 220

Val Arg Arg Leu Leu Gly Ile Ala Val Cys Leu Gly Ser Thr Trp Tyr
225                 230                 235                 240

Thr Thr Val Pro Met Phe Trp Cys Ala Ala Thr Tyr Tyr Ala Thr Ser
                245                 250                 255

Ser Gly Phe Phe Gln Leu Ile Val Gly Glu Arg Asn Phe Arg Val Ser
            260                 265                 270

Ser Leu Ser Trp Ser Val Val Arg Leu Pro Val Val Pro
        275                 280                 285
```

```
<210> SEQ ID NO 8
<211> LENGTH: 20
<212> TYPE: PRT
<213> ORGANISM: Chlamydia trachomatis

<400> SEQUENCE: 8

Ala Gln Gly Lys Leu Ile Val Thr Asn Pro Lys Ser Asp Ile Ser Phe
 1               5                  10                  15

Gly Gly Arg Val
            20

<210> SEQ ID NO 9
<211> LENGTH: 20
<212> TYPE: PRT
<213> ORGANISM: Chlamydia trachomatis

<400> SEQUENCE: 9

Lys Ser Asp Ile Ser Phe Gly Gly Arg Val Asn Leu Ala Asp Asn Thr
 1               5                  10                  15

Val Asn Tyr Ser
            20

<210> SEQ ID NO 10
<211> LENGTH: 173
<212> TYPE: PRT
<213> ORGANISM: Chlamydia trachomatis

<400> SEQUENCE: 10

Met Lys Lys Phe Leu Leu Leu Ser Leu Met Ser Leu Ser Ser Leu Pro
 1               5                  10                  15

Thr Phe Ala Ala Asn Ser Thr Gly Thr Ile Gly Ile Val Asn Leu Arg
            20                  25                  30

Arg Cys Leu Glu Glu Ser Ala Leu Gly Lys Lys Glu Ser Ala Glu Phe
        35                  40                  45

Glu Lys Met Lys Asn Gln Phe Ser Asn Ser Met Gly Lys Met Glu Glu
    50                  55                  60

Glu Leu Ser Ser Ile Tyr Ser Lys Leu Gln Asp Asp Tyr Met Glu
65                  70                  75                  80

Gly Leu Ser Glu Thr Ala Ala Ala Glu Leu Arg Lys Lys Phe Glu Asp
                85                  90                  95

Leu Ser Ala Glu Tyr Asn Thr Ala Gln Gly Gln Tyr Tyr Gln Ile Leu
            100                 105                 110

Asn Gln Ser Asn Leu Lys Arg Met Gln Lys Ile Met Glu Glu Val Lys
        115                 120                 125

Lys Ala Ser Glu Thr Val Arg Ile Gln Glu Gly Leu Ser Val Leu Leu
    130                 135                 140

Asn Glu Asp Ile Val Leu Ser Ile Asp Ser Ser Ala Asp Lys Thr Asp
145                 150                 155                 160

Ala Val Ile Lys Val Leu Asp Asp Ser Phe Gln Asn Asn
                165                 170

<210> SEQ ID NO 11
<211> LENGTH: 9
<212> TYPE: PRT
<213> ORGANISM: Chlamydia trachomatis

<400> SEQUENCE: 11

Tyr Gln Ile Leu Asn Gln Ser Asn Leu
```

<210> SEQ ID NO 12
<211> LENGTH: 9
<212> TYPE: PRT
<213> ORGANISM: Chlamydia trachomatis

<400> SEQUENCE: 12

Leu Asn Gln Ser Asn Leu Lys Arg Met
1               5

<210> SEQ ID NO 13
<211> LENGTH: 1531
<212> TYPE: PRT
<213> ORGANISM: Chlamydia trachomatis

<400> SEQUENCE: 13

Met Ser Ser Glu Lys Asp Ile Lys Ser Thr Cys Ser Lys Phe Ser Leu
1               5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45

Gly Pro Gln Ala Val Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln

```
           305                 310                 315                 320
Asn Cys Ala Glu Leu Val Phe Lys Gly Asn Cys Ala Ile Gly Thr Glu
                325                 330                 335
Asp Lys Gly Ser Leu Gly Gly Ala Ile Ser Ser Leu Gly Thr Val
                340                 345                 350
Leu Leu Gln Gly Asn His Gly Ile Thr Cys Asp Lys Asn Glu Ser Ala
                355                 360                 365
Ser Gln Gly Gly Ala Ile Phe Gly Lys Asn Cys Gln Ile Ser Asp Asn
        370                 375                 380
Glu Gly Pro Val Val Phe Arg Asp Ser Thr Ala Cys Leu Gly Gly
385                 390                 395                 400
Ala Ile Ala Ala Gln Glu Ile Val Ser Ile Gln Asn Asn Gln Ala Gly
                405                 410                 415
Ile Ser Phe Glu Gly Gly Lys Ala Ser Phe Gly Gly Ile Ala Cys
                420                 425                 430
Gly Ser Phe Ser Ser Ala Gly Gly Ala Ser Val Leu Gly Thr Ile Asp
        435                 440                 445
Ile Ser Lys Asn Leu Gly Ala Ile Ser Phe Ser Arg Thr Leu Cys Thr
    450                 455                 460
Thr Ser Asp Leu Gly Gln Met Glu Tyr Gln Gly Gly Ala Leu Phe
465                 470                 475                 480
Gly Glu Asn Ile Ser Leu Ser Glu Asn Ala Gly Val Leu Thr Phe Lys
                485                 490                 495
Asp Asn Ile Val Lys Thr Phe Ala Ser Asn Gly Lys Ile Leu Gly Gly
                500                 505                 510
Gly Ala Ile Leu Ala Thr Gly Lys Val Glu Ile Thr Asn Asn Ser Glu
        515                 520                 525
Gly Ile Ser Phe Thr Gly Asn Ala Arg Ala Pro Gln Ala Leu Pro Thr
        530                 535                 540
Gln Glu Glu Phe Pro Leu Phe Ser Lys Lys Glu Gly Arg Pro Leu Ser
545                 550                 555                 560
Ser Gly Tyr Ser Gly Gly Ala Ile Leu Gly Arg Glu Val Ala Ile
                565                 570                 575
Leu His Asn Ala Ala Val Val Phe Glu Gln Asn Arg Leu Gln Cys Ser
                580                 585                 590
Glu Glu Glu Ala Thr Leu Leu Gly Cys Cys Gly Gly Ala Val His
        595                 600                 605
Gly Met Asp Ser Thr Ser Ile Val Gly Asn Ser Ser Val Arg Phe Gly
        610                 615                 620
Asn Asn Tyr Ala Met Gly Gln Gly Val Ser Gly Ala Leu Leu Ser
625                 630                 635                 640
Lys Thr Val Gln Leu Ala Gly Asn Gly Ser Val Asp Phe Ser Arg Asn
                645                 650                 655
Ile Ala Ser Leu Gly Gly Ala Leu Gln Ala Ser Glu Gly Asn Cys
                660                 665                 670
Glu Leu Val Asp Asn Gly Tyr Val Leu Phe Arg Asp Asn Arg Gly Arg
        675                 680                 685
Val Tyr Gly Gly Ala Ile Ser Cys Leu Arg Gly Asp Val Val Ile Ser
        690                 695                 700
Gly Asn Lys Gly Arg Val Glu Phe Lys Asp Asn Ile Ala Thr Arg Leu
705                 710                 715                 720
Tyr Val Glu Glu Thr Val Glu Lys Val Glu Val Glu Pro Ala Pro
                725                 730                 735
```

```
Glu Gln Lys Asp Asn Glu Leu Ser Phe Leu Gly Arg Ala Glu Gln
              740                 745                 750

Ser Phe Ile Thr Ala Ala Asn Gln Ala Leu Phe Ala Ser Glu Asp Gly
              755                 760                 765

Asp Leu Ser Pro Glu Ser Ser Ile Ser Ser Glu Leu Ala Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
                820                 825                 830

Gly Gln Ile Pro Glu Val Leu Ile Ser Gly Asn Ala Gly Asp Val Val
            835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Gly Ala Val Arg
                885                 890                 895

Ile Glu Asp His Gly Asn Val Leu Leu Glu Ala Phe Gly Gly Asp Ile
                900                 905                 910

Val Phe Lys Gly Asn Ser Ser Phe Arg Ala Gln Gly Ser Asp Ala Ile
            915                 920                 925

Tyr Phe Ala Gly Lys Glu Ser His Ile Thr Ala Leu Asn Ala Thr Glu
    930                 935                 940

Gly His Ala Ile Val Phe His Asp Ala Leu Val Phe Glu Asn Leu Glu
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
            980                 985                 990

Gln Cys Ile His Val Gln Gln Gly Ser Leu Glu Leu Leu Asn Gly Ala
        995                 1000                1005

Thr Leu Cys Ser Tyr Gly Phe Lys Gln Asp Ala Gly Ala Lys Leu
    1010                1015                1020

Val Leu Ala Ala Gly Ala Lys Leu Lys Ile Leu Asp Ser Gly Thr
    1025                1030                1035

Pro Val Gln Gln Gly His Ala Ile Ser Lys Pro Glu Ala Glu Ile
    1040                1045                1050

Glu Ser Ser Ser Glu Pro Gly Ala His Ser Leu Trp Ile Ala
    1055                1060                1065

Lys Asn Ala Gln Thr Thr Val Pro Met Val Asp Ile His Thr Ile
    1070                1075                1080

Ser Val Asp Leu Ala Ser Phe Ser Ser Ser Gln Gln Glu Gly Thr
    1085                1090                1095

Val Glu Ala Pro Gln Val Ile Val Pro Gly Gly Ser Tyr Val Arg
    1100                1105                1110

Ser Gly Glu Leu Asn Leu Glu Leu Val Asn Thr Thr Gly Thr Gly
    1115                1120                1125

Tyr Glu Asn His Ala Leu Leu Lys Asn Glu Ala Lys Val Pro Leu
    1130                1135                1140
```

```
Met Ser Phe Val Ala Ser Gly Asp Glu Ala Ser Ala Glu Ile Ser
1145                1150                1155
Asn Leu Ser Val Ser Asp Leu Gln Ile His Val Val Thr Pro Glu
1160                1165                1170
Ile Glu Glu Asp Thr Tyr Gly His Met Gly Asp Trp Ser Glu Ala
1175                1180                1185
Lys Ile Gln Asp Gly Thr Leu Val Ile Ser Trp Asn Pro Thr Gly
1190                1195                1200
Tyr Arg Leu Asp Pro Gln Lys Ala Gly Ala Leu Val Phe Asn Ala
1205                1210                1215
Leu Trp Glu Glu Gly Ala Val Leu Ser Ala Leu Lys Asn Ala Arg
1220                1225                1230
Phe Ala His Asn Leu Thr Ala Gln Arg Met Glu Phe Asp Tyr Ser
1235                1240                1245
Thr Asn Val Trp Gly Phe Ala Phe Gly Gly Phe Arg Thr Leu Ser
1250                1255                1260
Ala Glu Asn Leu Val Ala Ile Asp Gly Tyr Lys Gly Ala Tyr Gly
1265                1270                1275
Gly Ala Ser Ala Gly Val Asp Ile Gln Leu Met Glu Asp Phe Val
1280                1285                1290
Leu Gly Val Ser Gly Ala Ala Phe Leu Gly Lys Met Asp Ser Gln
1295                1300                1305
Lys Phe Asp Ala Glu Val Ser Arg Lys Gly Val Val Gly Ser Val
1310                1315                1320
Tyr Thr Gly Phe Leu Ala Gly Ser Trp Phe Phe Lys Gly Gln Tyr
1325                1330                1335
Ser Leu Gly Glu Thr Gln Asn Asp Met Lys Thr Arg Tyr Gly Val
1340                1345                1350
Leu Gly Glu Ser Ser Ala Ser Trp Thr Ser Arg Gly Val Leu Ala
1355                1360                1365
Asp Ala Leu Val Glu Tyr Arg Ser Leu Val Gly Pro Val Arg Pro
1370                1375                1380
Thr Phe Tyr Ala Leu His Phe Asn Pro Tyr Val Glu Val Ser Tyr
1385                1390                1395
Ala Ser Met Lys Phe Pro Gly Phe Thr Glu Gln Gly Arg Glu Ala
1400                1405                1410
Arg Ser Phe Glu Asp Ala Ser Leu Thr Asn Ile Thr Ile Pro Leu
1415                1420                1425
Gly Met Lys Phe Glu Leu Ala Phe Ile Lys Gly Gln Phe Ser Glu
1430                1435                1440
Val Asn Ser Leu Gly Ile Ser Tyr Ala Trp Glu Ala Tyr Arg Lys
1445                1450                1455
Val Glu Gly Gly Ala Val Gln Leu Leu Glu Ala Gly Phe Asp Trp
1460                1465                1470
Glu Gly Ala Pro Met Asp Leu Pro Arg Gln Glu Leu Arg Val Ala
1475                1480                1485
Leu Glu Asn Asn Thr Glu Trp Ser Ser Tyr Phe Ser Thr Val Leu
1490                1495                1500
Gly Leu Thr Ala Phe Cys Gly Gly Phe Thr Ser Thr Asp Ser Lys
1505                1510                1515
Leu Gly Tyr Glu Ala Asn Thr Gly Leu Arg Leu Ile Phe
1520                1525                1530
```

```
<210> SEQ ID NO 14
<211> LENGTH: 8
<212> TYPE: PRT
<213> ORGANISM: Chlamydia trachomatis

<400> SEQUENCE: 14

Phe Ser Val Thr Asn Pro Trp Phe
1               5

<210> SEQ ID NO 15
<211> LENGTH: 20
<212> TYPE: PRT
<213> ORGANISM: Chlamydia trachomatis

<400> SEQUENCE: 15

Asn Val Thr Gln Asp Leu Thr Ser Ser Thr Ala Lys Leu Glu Cys Thr
1               5                   10                  15

Gln Asp Leu Ile
            20

<210> SEQ ID NO 16
<211> LENGTH: 20
<212> TYPE: PRT
<213> ORGANISM: Chlamydia trachomatis

<400> SEQUENCE: 16

Ala Lys Leu Glu Cys Thr Gln Asp Leu Ile Ala Gln Gly Lys Leu Ile
1               5                   10                  15

Val Thr Asn Pro
            20

<210> SEQ ID NO 17
<211> LENGTH: 9
<212> TYPE: PRT
<213> ORGANISM: Chlamydia trachomatis

<400> SEQUENCE: 17

Ser Asn Leu Lys Arg Met Gln Lys Ile
1               5

<210> SEQ ID NO 18
<211> LENGTH: 9
<212> TYPE: PRT
<213> ORGANISM: Chlamydia trachomatis

<400> SEQUENCE: 18

Ala Ala Leu Tyr Ser Thr Glu Asp Leu
1               5

<210> SEQ ID NO 19
<211> LENGTH: 9
<212> TYPE: PRT
<213> ORGANISM: Chlamydia trachomatis

<400> SEQUENCE: 19

Phe Gln Glu Lys Asp Ala Asp Thr Leu
1               5

<210> SEQ ID NO 20
<211> LENGTH: 9
<212> TYPE: PRT
<213> ORGANISM: Chlamydia trachomatis

<400> SEQUENCE: 20
```

```
Gln Ser Val Asn Glu Leu Val Tyr Val
1               5

<210> SEQ ID NO 21
<211> LENGTH: 9
<212> TYPE: PRT
<213> ORGANISM: Chlamydia trachomatis

<400> SEQUENCE: 21

Leu Glu Phe Ala Ser Cys Ser Ser Leu
1               5

<210> SEQ ID NO 22
<211> LENGTH: 9
<212> TYPE: PRT
<213> ORGANISM: Chlamydia trachomatis

<400> SEQUENCE: 22

Ser Gln Ala Glu Gly Gln Tyr Arg Leu
1               5

<210> SEQ ID NO 23
<211> LENGTH: 9
<212> TYPE: PRT
<213> ORGANISM: Chlamydia trachomatis

<400> SEQUENCE: 23

Gly Gln Ser Val Asn Glu Leu Val Tyr
1               5

<210> SEQ ID NO 24
<211> LENGTH: 9
<212> TYPE: PRT
<213> ORGANISM: Chlamydia trachomatis

<400> SEQUENCE: 24

Gln Ala Val Leu Leu Leu Asp Gln Ile
1               5
```